US008815953B2

(12) United States Patent
Salentine et al.

(10) Patent No.: US 8,815,953 B2
(45) Date of Patent: Aug. 26, 2014

(54) FORMULATIONS OF VITAMIN K ANALOGS FOR TOPICAL USE

(75) Inventors: Christopher G. Salentine, San Rafael, CA (US); Kieran O'Donoghue, San Mateo, CA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 478 days.

(21) Appl. No.: 12/381,467

(22) Filed: Mar. 12, 2009

(65) Prior Publication Data

US 2009/0234022 A1    Sep. 17, 2009

Related U.S. Application Data

(60) Provisional application No. 61/069,218, filed on Mar. 13, 2008, provisional application No. 61/204,939, filed on Jan. 13, 2009.

(51) Int. Cl.
*A61K 31/12* (2006.01)

(52) U.S. Cl.
USPC ...................................................... 514/681

(58) Field of Classification Search
None
See application file for complete search history.

(56) References Cited

U.S. PATENT DOCUMENTS

| | | | |
|---|---|---|---|
| 4,294,852 A | 10/1981 | Wildnauer et al. | |
| 4,374,775 A | 2/1983 | Dotz | |
| 4,719,239 A | 1/1988 | Muller et al. | |
| 4,840,970 A | 6/1989 | Ohasi et al. | |
| 4,906,411 A | 3/1990 | Shinnaka et al. | |
| 4,966,779 A | 10/1990 | Kirk | |
| 5,134,127 A | 7/1992 | Stella et al. | |
| 5,155,031 A | 10/1992 | Posner et al. | |
| 5,180,747 A | 1/1993 | Matsuda et al. | |
| 5,356,636 A | 10/1994 | Schneider et al. | |
| 5,376,645 A | 12/1994 | Stella et al. | |
| 5,412,125 A | 5/1995 | Philippe et al. | |
| 5,510,391 A | 4/1996 | Elson | |
| 5,637,741 A | 6/1997 | Matsumoto et al. | |
| 5,643,583 A | 7/1997 | Voultoury et al. | |
| 5,650,156 A | 7/1997 | Grinstaff et al. | |
| 5,770,774 A | 6/1998 | Joo et al. | |
| 5,785,976 A | 7/1998 | Westesen et al. | |
| 5,885,486 A | 3/1999 | Westesen et al. | |
| 5,916,749 A | 6/1999 | Bandman et al. | |
| 6,013,665 A | 1/2000 | DeMichele et al. | |
| 6,110,891 A | 8/2000 | Pusztai et al. | |
| 6,160,007 A | 12/2000 | DeMichele et al. | |
| 6,187,822 B1 | 2/2001 | Leibovich | |
| 6,207,176 B1 | 3/2001 | Howard et al. | |
| 6,264,986 B1 | 7/2001 | Hahnlein et al. | |
| 6,383,471 B1 | 5/2002 | Chen et al. | |
| 6,426,078 B1 | 7/2002 | Bauer et al. | |
| 6,428,949 B1 | 8/2002 | Bandman et al. | |
| 6,524,594 B1 | 2/2003 | Santora et al. | |
| 6,537,579 B1 | 3/2003 | Desai et al. | |
| 6,576,660 B1 | 6/2003 | Liao et al. | |
| 6,579,994 B2 | 6/2003 | Sankarasubbier et al. | |
| 6,582,710 B2 | 6/2003 | Deckers et al. | |
| 6,596,287 B2 | 7/2003 | Deckers et al. | |
| 6,599,513 B2 | 7/2003 | Deckers et al. | |
| 6,660,306 B2 | 12/2003 | Peshoff | |
| 6,696,484 B2 | 2/2004 | Liao et al. | |
| 6,774,100 B2 | 8/2004 | Vishnupad | |
| 6,780,439 B2 | 8/2004 | Wilk | |
| 6,979,454 B1 | 12/2005 | Lindahl et al. | |
| 7,094,431 B2 | 8/2006 | Peshoff | |
| 7,252,816 B1 * | 8/2007 | Angel et al. | 424/59 |
| 7,326,690 B2 | 2/2008 | Henry et al. | |
| 7,402,557 B2 | 7/2008 | Miller et al. | |
| 7,405,188 B2 | 7/2008 | Chen | |
| 2002/0061304 A1 | 5/2002 | Miller et al. | |
| 2003/0139353 A1 | 7/2003 | Jackson et al. | |
| 2003/0158165 A1 | 8/2003 | Wilk | |
| 2003/0170187 A1 | 9/2003 | Marchal | |
| 2004/0004001 A1 | 1/2004 | Cohen et al. | |
| 2004/0047852 A1 | 3/2004 | Kennedy | |
| 2004/0062817 A1 | 4/2004 | Peshoff | |
| 2004/0081674 A1 | 4/2004 | Franke | |
| 2004/0138218 A1 | 7/2004 | Pallen et al. | |
| 2004/0265396 A1 | 12/2004 | Peshoff | |
| 2005/0048008 A1 | 3/2005 | Gupta | |
| 2005/0092969 A1 | 5/2005 | Ueda et al. | |
| 2005/0118187 A1 | 6/2005 | Yu | |
| 2005/0148521 A1 | 7/2005 | Ben-Sasson et al. | |

(Continued)

FOREIGN PATENT DOCUMENTS

DE    3514724 A1    10/1986
DE    10003786 A1    8/2001

(Continued)

OTHER PUBLICATIONS

Perez-Soler et al (J Clin Oncol 24(18S (Jun. 20 Suppl)):3036, 2006).*
Swarbrick et al (Encyclopedia of pharmaceutical technology, p. 2, 2002).*
Smolinske (Handbook of food, drug and cosmetic excipients, p. 47, 1992).*
Jian-Hwa Guo (Drug Delivery Technology, vol. 6, 2003).*
US Dept. Health and Human Services (Guidance for Industry, 1999).*
Abdelmohsen, Kotb et al., "Epidermal Growth Factor Receptor Is a Common Mediator of Quinone-induced Signaling Leading to Phosphorylation of Connexin-43," *The Journal of Biological Chemistry*, vol. 278(40):38360-38367 (2003).
Bae, Eun Young et al., "A New VHR Dual-Specificity Protein Tyrosine Phosphatase Inhibitor from *Dendrobium moniliforme*," *Planta Med.*, vol. 70:869-870 (2004).

(Continued)

*Primary Examiner* — Craig Ricci
(74) *Attorney, Agent, or Firm* — K&L Gates LLP; Louis C. Cullman; Hal Gibson

(57) ABSTRACT

The present invention provides topical formulations containing a vitamin K analog, e.g., menadione, that deliver a uniform, therapeutically effective concentration of the vitamin K analog to the skin in a vehicle which is stable, non-irritating, non-drying and cosmetically acceptable. These topical formulations are useful for the treatment and prevention of dermatological conditions associated with inflammation, particularly, dermatological conditions resulting from anti-EGFR therapies.

10 Claims, No Drawings

(56) References Cited

U.S. PATENT DOCUMENTS

| | | | |
|---|---|---|---|
| 2006/0002439 | A1 | 1/2006 | Lee |
| 2006/0058398 | A1 | 3/2006 | Kamei et al. |
| 2006/0216342 | A1 | 9/2006 | Torchilin et al. |
| 2006/0275504 | A1 | 12/2006 | Chen |
| 2007/0025950 | A1 | 2/2007 | Elson |
| 2007/0142462 | A1 | 6/2007 | Kennedy |
| 2007/0238697 | A1 | 10/2007 | Jackson et al. |

FOREIGN PATENT DOCUMENTS

| | | |
|---|---|---|
| EP | 0392845 A2 | 10/1990 |
| EP | 1214930 B1 | 6/2002 |
| JP | 2002-517436 | 6/2002 |
| JP | 2004-500392 | 1/2004 |
| JP | 2005-206521 | 8/2005 |
| WO | WO-94/23023 A1 | 10/1994 |
| WO | WO-97/39746 A1 | 10/1997 |
| WO | 99/63982 A1 | 12/1999 |
| WO | 01/67896 A2 | 9/2001 |
| WO | WO-01/64214 A2 | 9/2001 |
| WO | WO-01/91740 A2 | 12/2001 |
| WO | WO-02/13780 A1 | 2/2002 |
| WO | WO-02/20525 A2 | 3/2002 |
| WO | WO-02/47642 A1 | 6/2002 |
| WO | WO-03/018033 A1 | 3/2003 |
| WO | WO-03/061566 A2 | 7/2003 |
| WO | WO-03/101415 A1 | 12/2003 |
| WO | WO-2004/019923 A1 | 3/2004 |
| WO | WO-2005/032523 A1 | 4/2005 |
| WO | WO-2006/029893 A2 | 3/2006 |
| WO | WO-2006/056889 A2 | 6/2006 |
| WO | WO-2006/107827 A1 | 10/2006 |
| WO | WO-2006/113479 A2 | 10/2006 |
| WO | WO-2007/147128 A2 | 12/2007 |
| WO | WO-2008/004231 A1 | 1/2008 |

OTHER PUBLICATIONS

Bernier, J. et al., "Consensus guidelines for the management of radiation dermatitis and coexisting acne-like rash in patients receiving radiotherapy plus EGFR inhibitors for the treatment of squamous cell carcinoma of the head and neck," *Annals of Oncology*, vol. 19(1):142-149 (2007).

Busam, K.J. et al., "Cutaneous side-effects in cancer patients treated with the antiepidermal growth factor receptor antibody C225," *British Journal of Dermatology*, vol. 144:1169-1176 (2001).

Cohen, Ezra E.W. et al., "Phase II Trial of ZD1839 in Recurrent or Metastatic Squamous Cell Carcinoma of the Head and Neck," *Journal of Clinical Oncology*, vol. 21(10):1980-1987 (2003).

deBeer, Edwin J. et al., "Routes of Administration of Materials Capable of Acting as Vitamin K," *Proc. Soc. Exp. Biol and Med.*, vol. 46:535-537 (1941).

Elson, Melvin L., "Topical Phytonadione (Vitamin $K_1$) in the Treatment of Actinic and Traumatic Purpura," *Cosmetic Dermatology*, vol. 8(12):25-27 (1995).

Gerling, Norbert et al., "The tyrosine phosphatase inhibitor orthovanadate mimics NGF-induced neuroprotective signaling in rat hippocampal neurons," *Neurochemistry International*, vol. 44:505-520 (2004).

Lage, Augustin et al., "Targeting epidermal growth factor receptor signaling: early results and future trends in oncology," *Annals of Medicine*, vol. 35(5):327-336 (2003).

Lee, Kyeong et al., "CD45 Protein-Tyrosine Phosphatase Inhibitor Development," *Current Topics in Medicinal Chemistry*, vol. 3:797-807 (2003).

Liem, David A. et al., "The Tyrosine Phosphatase Inhibitor Bis(Maltolato)-Oxovanadium Attenuates Myocardial Reperfusion Injury by Opening ATP-Sensitive Potassium Channels," *The Journal of Pharmacology and Experimental Therapeutics*, vol. 309(3):1256-1262 (2004).

LoRusso, Patricia M., "Phase I Studies of ZD1839 in Patients With Common Solid Tumors," *Seminars in Oncology*, vol. 30(1, Suppl. 1):21-29 (2003).

Lou, Wendy W. et al., "Effects of Topical Vitamin K and Retinol on Laser-Induced Purpura on Nonlesional Skin," *Dermatol. Surg.*, vol. 25:942-944 (1999).

Matschiner, John T. et al., "Metabolism and Vitamin K Activity of *cis* Phylloquinone in Rats," *J. Nutrition*, vol. 102:625-630 (1972).

Page, R.C. et al., "Dermatitis from Topical Application of 2-Methyl-1:4-Naphthoqunone (Synthetic Vitamin K Analogue)," *The American Journal of the Medical Sciences*, vol. 203:566-569 (1942).

Russell, H.K. et al., "Effect of Topical Application of 2-Methyl-1,4-Naph-Thoquinone (Synthetic Vitamin K Analogue) on the Prothrombin Level of Newborn Infants. With Reference to a Simplified Micro-prothrombin Test," *Am. J. Med. Sci.*, vol. 202:355-359 (1941).

Sah, Peter P.T., "Synthesis of 3-Methyl-4-Amino-1-naphthol hydrochloride (vitamin K) and related vitamin-K-active compounds," *Zeitschrift für Vitamin-, Hormon- und Fermentforschung*, vol. 3(3-4):324-345 (1949-1950).

Shah, Neha S. et al., "The effects of topical vitamin K on bruising after laser treatment," *J. Am. Acad. Dermatol.*, vol. 47:241-244 (2002).

Susman, Ed, "Rash correlates with tumour response after cetuximab," *The Lancet, Oncology*, vol. 5:647 (2004).

Ulbrich, A.P., "Topical application of menadione, a synthetic vitamin K: Preliminary report," *J Am. Osteopathic Assoc.*, vol. 60:370-374 (1961).

Vanhoefer, Udo et al., "Phase I Study of the Humanized Antiepidermal Growth Factor Receptor Monoclonal Antibody EMD72000 in Patients With Advanced Solid Tumors That Express the Epidermal Growth Factor Receptor," *J. Clin. Oncol.*, vol. 22:175-184 (2004).

Adachi, T. et al., "PP1390 Mechanism of antitumor action of Menadione (Vitamine K3)," Nihon Gekagakkai Zasshi (J. Japan Surgical Soc.) vol. 103, Special Issue, p. 654 (2002).

Baselga, J. et al., "Phase I Safety, Pharmacokinetic, and Pharmacodynamic Trial of ZD1839, a Selective Oral Epidermal Growth Factor Receptor Tyrosine Kinase Inhibitor, in Patients With Five Selected Solid Tumor Types," Journal of Clinical Oncology, vol. 20(21):4292-4302 (2002).

Clark, G.M. et al., "Rash severity is predictive of increased survival with erlotinib HCl," Proceedings of the American Society of Clinical Oncology, vol. 22, Abstr. No. 786 (2003).

Guo, Jian-Hwa, "Excipient Update," Carbopol Polymers for Pharmaceutical Drug Delivery Applications, vol. 6 (2003).

Jacot, W. et al., "Acneiform eruption induced by epidermal growth factor receptor inhibitors in patients with solid tumours," British Journal of Dermatology, vol. 151:232-257 (2004).

Lacouture, Mario E., "Insights Into the Pathophysiology and Management of Dermatologic Toxicities to EGFR-Targeted Therapies in Colorectal Cancer," Cancer Nursing, vol. 30(4S):517-526 (2007).

Nannery, Lillian B. et al., "Immunolocalization of Epidermal Growth Factor Receptors in Normal Developing Human Skin," J. Invest. Dermatol., vol. 94:742-748 (1990).

Osada, Shinji et al., "New Approach to Cancer Therapy: The Application of Signal Transduction to Anti-Cancer Drug," Curr. Med. Chem., vol. 3:119-131 (2003).

Perea, Sofia et al., "Predictors of Sensitivity and Resistance to Epidermal Growth Factor Receptor Inhibitors," Clinical Lung Cancer, vol. 6(Suppl. 1):S30-S34 (2004).

Perez-Soler, Roman et al., "Can Rash Associated With HER1/EGFR Inhibition Be Used as a Marker of Treatment Outcome?" Oncology, vol. 17(11):1-6 (2003).

Perez-Soler, Roman et al., "HER1/EGFR Inhibitor-Associated Rash: Future Directions for Management and Investigation Outcomes from the HER1/EGFR Inhibitor Rash Management Forum," The Oncologist, vol. 10:345-356 (2005).

Potthoff, K. et al., "Interdisciplinary management of EGFR-inhibitor-induced skin reactions: a German expert opinion," Annals of Oncology, vol. 22:524-535 (2011).

Rodeck, Ulrich et al., "EGF-R dependent regulation of keratinocyte survival," Journal of Cell Science, vol. 110:113-121 (1997).

(56) References Cited

OTHER PUBLICATIONS

Saltz, Leonard B. et al., "Phase II Trial of Cetuximab in Patients With Refractory Colorectal Cancer That Expresses the Epidermal Growth Factor Receptor," Journal of Clinical Oncology, vol. 22(7):1201-1208 (2004).

Saltz, L. et al., "The presence and intensity of the cetuximab-induced acne-like rash predicts increased survival in studies across multiple malignancies," Proceedings of the American Society of Clinical Oncology, vol. 22, Abstr. No. 817 (2003).

Satoh, Yachiyo et al., "Drug eruption due to gefitinib (IRESSA)," Rinsho Hifuka (Clinical Dermatology) vol. 58 (5):28-32 (2004).

Smolinske, Susan C., "Benzyl Alcohol," Handbook of Food, Drug, and Cosmetic Excipients, p. 47 (1992).

Sorg, Olivier et al., "Oxidative Stress-Independent Depletion of Epidermal Vitamin A by UVA," J. Invest. Dermatol., vol. 118:513-518 (2002).

Soulieres, Denis et al., "Multicenter PHase II Study of Erlotinib, an Oral Epidermal Growth Factor Receptor Tyrosine Kinase Inhibitor, in Patients With Recurrent or Metastatic Squamous Cell Cancer of the Head and Neck," Journal of Clinical Oncology, vol. 22(1):77-85 (2004).

Swarbrick, James et al., Encyclopedia of Pharmaceutical Technology, Second Edition, vol. 1, p. 2 (2002).

Van Doorn, R. et al., "Follicular and epidermal alterations in patients treated with ZD1839 (Iressa), an inhibitor of the epidermal growth factor receptor," British Journal of Dermatology, vol. 147:598-601 (2002).

European Summons to Attend Oral Proceedings for Application No. 06750246.8, 6 pages, dated Apr. 4, 2012.

European Office Action for Application No. 10195772.8, 8 pages, dated Nov. 15, 2011.

International Preliminary Report on Patentability for Application No. PCT/US2006/014158, dated Oct. 16, 2007.

Internationanl Preliminary Report on Patentability for Application No. PCT/US2009/037041, 18 pages, dated Mar. 17, 2010.

International Search Report for Application No. PCT/US06/14158, dated Feb. 16, 2007.

International Search Report and Written Opinion for Application No. PCT/US2009/037041, 18 pages, dated Jun. 23, 2009.

Japanese Office Action for Application No. JP2008-506765, 15 pages, dated Mar. 6, 2012.

* cited by examiner

FORMULATIONS OF VITAMIN K ANALOGS FOR TOPICAL USE

RELATED APPLICATIONS

This application claim priority to U.S. Provisional Application No. 61/069,218, titled "EMULSIONS OF VITAMIN K ANALOGS FOR TOPICAL USE", filed Mar. 13, 2008 and to U.S. Provisional Application No. 61/204,939, titled "EMULSIONS OF VITAMIN K ANALOGS FOR TOPICAL USE", filed Jan. 13, 2009, the entire contents of which are incorporated herein by this reference.

BACKGROUND OF THE INVENTION

Epidermal growth factor (EGF), acting through its receptor EGFR, is a mitogen and survival factor for keratinocytes and other epithelial cells (Rheinwald et al. Nature, 1997: 265:421; Rodeck et al. J. Cell Science, 1997; 110:113). It is crucial for the normal development and physiology of the epidermis. Inhibition of EGFR can result in abnormal proliferation, migration and premature differentiation of basal keratinocytes as demonstrated by upregulated p27KIP1, KRT1 and STAT3 in the basal layer, and consequent disruption of the integrity of the skin with the recruitment of inflammatory cells (Jost et al. Eur. J. Dermatol. 2000; 10:505-510; Lacouture, Nat. Rev. Cancer 2006; 6:803-812).

Agents that inhibit EGFR have been shown to be active antitumor agents against a variety of solid tumors including but not limited to colorectal carcinoma, non-small cell lung cancer, head and neck cancer and malignant gliomas (Conen et al., 2003; Lage et a!., 2003; Lorusso, 2003; Vanhoefer et al., 2004). Clinical benefit, defined as relief of symptoms or prolongation of survival, has been so far demonstrated with the anti-EGFR antibody cetuximab (Erbitux®) and the EGFR tyrosine kinase (TK) inhibitors gefitinib (Iressa®) and erlotinib (Tarceva®).

In addition, EGFR inhibitors are increasingly being used in a range of tumor types in combination with standard therapies in an attempt to improve outcome. In 2006, results of a randomized phase III study demonstrated that the addition of the EGFR-targeted IgG1 mAb, cetuximab, to radiotherapy resulted in statistically significant and clinically meaningful improvements in the duration of locoregional control and median overall survival versus radiotherapy alone in the treatment of locoregionally advanced squamous cell carcinoma of the head and neck (Bonner al. N. Engl. J. Med. 2006; 354: 567-578).

Although EGFR inhibitors do not cause life threatening toxicities, their use can be associated with the development of skin reactions, including a macular, papular, pustular rash, commonly referred to as acne-like rash (or folliculitis); xerosis; fissures; telangiectasia; hyperpigmentation; and hair and nail changes (Segaert et al. Ann. Oncol. 2005; 16:1425-1433). In addition, inflammation is commonly found in the epidermal-dermal junction, accompanied by neutrophilic infiltration and damage to the hair follicles.

The most common skin reaction, the acne-like rash which occurs in 60-70% of patients, is generally distributed in areas rich with sebaceous glands, such as the face, neck and retroauricular area, the shoulders, the upper trunk and the scalp. Main symptoms caused by the skin rash, itching, dryness, and secondary infection, cause discomfort and unfavorable cosmetic changes in many cases. The occurrence and intensity of the rash are clearly dose-related and the median time of occurrence is 10 days after initiation of therapy and peaks after 2-3 weeks. In some cases, the rash can be delayed, and in others flares can occur at each subsequent, administration of the EGFR inhibitor. In addition, abnormalities in hair growth especially the scalp and eyelashes have been reported in approximately 20% of patients, and periungual inflammation with tenderness in about 15% (Lacouture, Nat. Rev. Cancer, 2006; 6:803-812). About 10% of patients discontinue therapy due to skin toxicity.

There is growing evidence that the skin rash is a surrogate indicator of antitumor efficacy and clinical benefit of anti-EGFR therapy (Cohen et al. J. Clin. Oncol., 2003; 21:1980-1987). Accordingly, increasing dosing of anti-EGFR agents to cause a skin rash may become a common practice and the effective treatment of the skin rash is also becoming of increasing importance. Topical or systemic antibiotics, anti-inflammatory agents, retinoids, topical lubricants, and other types of remedies have been tried in an empirical fashion with poor or inconsistent results. More recently, the topical application of menadione (vitamin K3), an EGFR phosphatase inhibitor, was shown to restore EGFR-mediated signaling in human skin secondary to systemic administration of the EGFR inhibitors, erlotinib and cetuximab (Ling et al. WO 2006/113479).

Accordingly, there is a need for effective topical formulations for the treatment and/or prevention of this EGFR-mediated skin conditions including epithelial toxicity associated with anti-EGFR therapy, a condition that is expected to affect more than 150,000 individuals each year in the USA alone.

SUMMARY OF THE INVENTION

The present invention demonstrates, inter alia, that topical formulations containing a vitamin K analog, e.g., menadione, deliver a uniform, therapeutically effective concentration of the vitamin K analog to the skin in a vehicle which is stable, non-irritating, non-drying and cosmetically acceptable. These topical formulations are useful for the treatment and prevention of dermatological conditions associated with inflammation, particularly, dermatological conditions resulting from anti-EGFR therapies.

Accordingly, in one aspect, the invention provides a topically applicable pharmaceutical formulation suitable for treatment of a dermatological condition comprising a vitamin K analog, a, i.e., one or more, lipophilic component, a, i.e., one or more, gelling agent, a, i.e., one or more, microbiological preservative, and water.

In one embodiment, the vitamin K analog contained in the pharmaceutical formulation of the invention activates EGFR. In another embodiment, the vitamin K analog is menadione, a drug substance for which a monograph exists in the United States Pharmacopeia (USP). In one embodiment, the formulation is ethyl alcohol free.

In related embodiments, the formulation comprises a sufficient amount of the vitamin K analog, or a sufficient composition independent of the vitamin K analog concentration, to deliver a concentration of 0.1 to 1.5 mM of the vitamin K analog to the epidermal skin layer when applied topically, or a concentration of 0.2 to 1.2 mM of the vitamin K analog when applied topically. In other related embodiments, the pharmaceutical formulation comprises from about 0.01% to 10% (w/w) of the vitamin K analog, from about 0.05% to 0.5% (w/w) of the vitamin K analog, from about 0.05% to 0.2% (w/w) of the vitamin K analog, about 0.05% (w/w) of the vitamin K analog, about 0.1% (w/w) of the vitamin K analog, or about 0.2% (w/w) of the vitamin K analog.

In another embodiment, the lipophilic component contained in the pharmaceutical formulation of the invention is selected from the group consisting of isopropyl myristate, caprylic/capric triglyceride, diethyl sebacate, diisopropyl adipate, petrolatum, mineral oil, and cyclomethicone.

In a related embodiment, the formulation comprises from about 1% to about 100% (w/w) of the lipophilic component. In another embodiment, the formulation comprises from about 1% to about 35% (w/w) of the lipophilic component. In yet another embodiment, the formulation comprises from about 3% to about 12% (w/w) of the lipophilic component.

In another embodiment, the pharmaceutical formulation of the invention contains from about 0.1 to 5% (w/w) of a gelling agent. In one embodiment, the gelling agent comprises one or more acrylic acid based polymers (e.g., Carbopol 981, Pemulen TR-1, or combinations thereof).

In another embodiment, the pharmaceutical formulation of the invention comprises from about zero % to 95% (w/w) water. In one embodiment, the formulation comprises from about 60% to 90% (w/w) water. In another embodiment, the formulation comprises from about 30% to 95% (w/w) water.

In further embodiments, the pharmaceutical formulation of the invention may contain a microbiological preservative if the formulation contains water. In one embodiment, the preservative is selected from the group consisting of benzyl alcohol, methylparaben and propylparaben. In related embodiments, the formulation contains from about 0.01 to 50% (w/w) of the preservative, or from about 0.01 to 5% (w/w) of the preservative. In other related embodiments, the formulation contains from about 0.1% to 5% benzyl alcohol, about 0.5% to, 5%, or about 1% benzyl alcohol.

In still other embodiments, the pharmaceutical formulation of the invention may also contain a neutralizing agent. In related embodiments, the neutralizing agent maintains the pH of the formulation at about 4.0 to 8.0, at about 5.0 to 6.5, or at about 5.5 to 6.0. In another embodiment, the neutralizing agent maintains the pH of the formulation at about 5.5.

In preferred embodiments, the pharmaceutical formulation of the invention is a cream or a lotion. In related embodiments, the formulation is a lotion having a viscosity at room temperature (25° C.) of approximately 1,000 to 20,000 cps, approximately 1,000 to 10,000, or approximately 3,000 to 4,000 cps.

In one preferred embodiment, the pharmaceutical formulation comprises: from about 0.01 to 10% (w/w) of menadione; from about 1 to 50% (w/w) of one or more lipophilic components; from about 0.01 to 5% (w/w) each of two different acrylic acid based polymers; from about 0.03 to 10% (w/w) of a preservative; a neutralizing agent sufficient to maintain a pH of about 4.0 to 7.0; and water.

In another preferred embodiment, the pharmaceutical formulation comprises: from about 0.05 to 2% (w/w) of menadione; from about 3 to 20% (w/w) of one or more lipophilic components; from about 0.1 to 1% (w/w) of an acrylic acid based polymer; from about 0.5 to 5% (w/w) of a preservative; a neutralizing agent sufficient to maintain a pH of about 4.5 to 6.5; and water.

In another preferred embodiment, the pharmaceutical formulation comprises: about 0.05% to 0.2% (w/w) menadione; about 12% (w/w) isopropyl myristate; about 0.3% (w/w) Pemulen TR-1; about 0.1% (w/w) Carbopol 981; about 1% (w/w) benzyl alcohol; sodium hydroxide sufficient to maintain a pH of about 5.0-6.0; and water.

In another preferred embodiment, the pharmaceutical formulation comprises: about 0.05% to 0.2% (w/w) menadione; about 3% (w/w) diethyl sebacate; about 0.3% (w/w) Pemulen TR-1; about 0.1% (w/w) Carbopol 981; about 0.3% (w/w) each of methylparaben and propylparaben; sodium hydroxide sufficient to maintain a pH of about 5.5 to 6.0; and water.

In another preferred embodiment, the pharmaceutical formulation comprises: about 0.05% to 0.2% (w/w) menadione; about 6% (w/w) diisopropyl adipate; about 0.3% (w/w) Pemulen TR-1; about 0.1% (w/w) Carbopol 981; about 0.3% (w/w) each of methylparaben and propylparaben; sodium hydroxide sufficient to maintain a pH of about 5.5; and water.

In another preferred embodiment, the pharmaceutical formulation comprises: about 0.05% to 0.2% (w/w) menadione; about 15% (w/w) diethyl sebacate; about 50% (w/w) isopropyl myristate; and about 35% (w/w) mineral oil.

In another preferred embodiment, the pharmaceutical formulation comprises: about 0.05% to 0.2% (w/w) menadione; about 15% (w/w) diethyl sebacate; about 10% (w/w) isopropyl myristate; about 65% (w/w) mineral oil; and about 10% cyclomethicone 5-NF.

In a related aspect, the invention also provides a packaged topically applicable pharmaceutical formulation suitable for treatment of a dermatological condition comprising a vitamin K analog, one or more lipophilic components, one or more gelling agents, one or more preservatives, and water in a light impermeable container. In one embodiment, the formulation is ethyl alcohol free.

In related embodiments of this aspect of the invention, the packaged formulation is chemically stable at a temperature of about 25° C. for at least about 3 months, at least about 6 months, at least about 9 months, or at least about 12 months. In one embodiment, the packaged pharmaceutical formulation is chemically stable in the temperature range of about 5° C. to 25° C. for at least about 3 months, at least about 6 months, at least about 9 months, or for at least about 12 months.

In another embodiment, the container is a compressible tube equipped with a blind end and a plastic cap composed of low-density or high-density polyethylene, polypropylene, or other similar polymers. Preferably the tube is composed of aluminum, and more preferably, the tube further comprises an internal lacquer coating.

In other embodiments, the container has from about a 10 to 200 g capacity, from about a 20 to 150 g capacity, from about 10-100 g, has about 30 g capacity or about 100 g capacity.

In still another embodiment, the packaged pharmaceutical formulation of the invention may also comprise an applicator, e.g., and LPDE applicator.

In another aspect, the invention provides a method of treating or preventing a dermatological condition comprising topically administering a therapeutically effective amount of a pharmaceutical formulation comprising a vitamin K analog, one or more lipophilic components, one or more gelling agents and/or dispersing agents, one or more preservatives, water, and other components as deemed appropriate. Alternatively, the formulation may comprise a vitamin K analog in a base of lipophilic components, without added water. The formulations of the invention may contain the vitamin K analog in a dissolved state or as a solid dispersion.

In one embodiment, the pharmaceutical formulation is administered topically at least once daily. In another embodiment, the pharmaceutical formulation is administered topically about one to four times daily. In one embodiment, the formulation is administered for about 3 days or about 4 days. In one embodiment the formulation is administered in about a 7-day cycle. In one embodiment, the formulation is administered in about a 7-day cycle over about a 28-day period.

In one embodiment, the dermatological conditions that may be treated according to the methods of the invention are associated with inflammation of the epidermis including, but not limited to skin rash, psoriasis, eczema, dermatitis, hair loss, and acne.

In a preferred embodiment, the dermatological condition is secondary to an anti-epidermal growth factor receptor (EGFR) therapy such as treatment with an anti-EGFR antibody (e.g., cetuximab) or with an EGFR tyrosine kinase inhibitor (e.g., gefitinib or erlotinib), and includes, but is not limited to, skin rash (e.g., acneform or macro-papular rash), hair follicle dysplasia, interfollicular epidermal hyperplasia, a failure or delay of wound healing and combinations thereof.

DETAILED DESCRIPTION

The instant invention is based, at least in part, on the discovery that a vitamin K analog, e.g., vitamin K3 (menadione), is compatible (e.g., physically and chemically stable) with various lipophilic components and incompatible with the majority of hydrophilic components tested. In particular, it has been discovered that formulations containing menadione, lipophilic components, gelling agents, preservatives, and water are capable of delivering therapeutically effective doses of menadione to the skin when topically administered.

Various aspects of the present invention are described in further detail in the following subsections.

I. Topical Formulations Containing Vitamin K Analogs

The topical formulations of the invention may be hydrophobic ointments, hydrophilic ointments, hydrophobic solutions, suspensions, sprays, or foams.

In one embodiment, the topical formulations of the invention are emulsions. A formulation, e.g., a topical emulsion, of the invention, in general, contains a vitamin K analog, a lipophilic component, a gelling agent and water. In one embodiment, the emulsions of the invention are ethyl alcohol free. Additional ingredients of the formulation may include, but are not limited to, preservatives, neutralizing agents, dispersing agents, antioxidants, UV-A and UV-B screening agents, topical anesthetics, polyol prepolymers, and phospholipids.

A pharmaceutical formulation, i.e., an emulsion, of the invention is formulated to deliver a therapeutically effective amount of the active ingredient, a vitamin K analog, to the epidermal layers of the skin when topically administered. The emulsion can be made using processes typical for the commercial manufacture of emulsions such as those described in the Examples set forth below. Preferably, the formulation is provided in the form of a cream or lotion and, preferably, is a lotion. In one embodiment, a lotion has the viscosity of approximately 3000 to 4000 cps. In another embodiment, the lotion has the viscosity of approximately 1000 to 10,000 cps.

In certain embodiments, a topical formulation of the invention is formulated to deliver a concentration of from about 0.1 to about 0.5 mM of the vitamin K analog to the epidermal layer of the skin when applied topically, e.g., does not permit penetration of the analog to deeper layers of the skin and/or to enter the circulation. In other embodiments, the formulation is formulated to deliver a concentration from about 0.2 to about 1.2 mM of a vitamin K analog to the epidermal skin layer when applied topically.

Typically, the formulation will comprise from about 0.01% to about 10% (w/w), from about 0.02 to about 2% (w/w), and preferably, from about 0.05 to about 0.5% (w/w) of the vitamin K analog. In one embodiment, the formulation contains from about 0.05 to about 0.2% (w/w) of the vitamin K analog. In one embodiment, the formulation comprises about 0.05% (w/w) of the vitamin K analog. In one embodiment, the formulation comprises about 0.1% (w/w) of the vitamin K analog. In one embodiment, the formulation comprises about 0.2% (w/w) of the vitamin K analog.

Vitamin K analogs that may be used in the formulation of the invention include any member of the vitamin K group, i.e., the group of naphthoquinone derivatives which can activate EGFR, Akt and/or Stat-3, or combinations thereof. As used herein, to "activate" EGFR, Akt and/or Stat-3 means to increase the phosphorylated form of EGFR, Akt and/or Stat-3. Examples of vitamin K analogs include, but are not limited to, vitamin K1 (2-methyl-3-phytyl-1,4-naphthoquinone), vitamin K2 (2-methyl-3-hexaprenyl-1,4-naphthoquinone; menaquinone), menadione (vitamin K3; 2-methyl-1,4-naphthoquinone), vitamin K4 (1,4-diacetoxy-2-methylnaphthalene), vitamin K5 (4-amino-2-methyl-1-naphthalenol), vitamin K6, vitamin K7 (3-methyl-4-amino-1-naphthol hydrochloride), menadione sodium bisulfite; menadione dimethylpyrimidinol bisulfite, analogs of the vitamin K group members having similar function, including but not limited to, dihydrovitamin K, menaquinone-4, menaquinone-6, menaquinone-7, menadiol, menadiol sodium diphosphate, menadiol diacetate, and menadoxime and its related salts; and compounds having the structure:

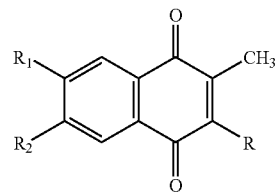

where R=H or a saturated or unsaturated aliphatic hydrocarbon; and R1 and R2H or CH3 which can activate EGFR, Akt and/or Stat-3.

In one embodiment, menadione is used in the formulation of the invention. menadione has the structure:

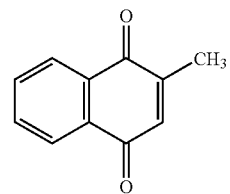

In another embodiment, the formulation of the invention contains Vitamin K1. Vitamin K1 has the structure:

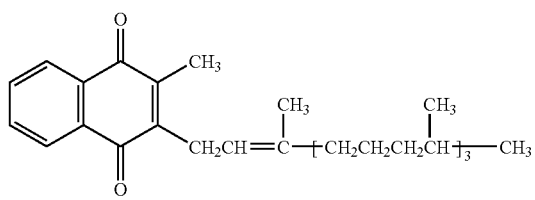

Preferred forms of vitamin K1 are the trans isomer of vitamin K1 or an admixture of the trans and cis isomers, since the cis isomer has little or no biological activity (Matschiner et al., 1972).

Vitamin K1 is present in many green leafy plants and vitamin K2 is produced by many intestinal bacteria. Vitamins K3, K4, K5, K6, and K7 are synthetic analogs. Processes have been described for preparing vitamin K analogs, e.g., U.S.

Pat. Nos. 4,374,775, 4,906,411, 5,412,124, 5,637,741, 5,770,774, and 6,579,994, and Sah (1949-50). Vitamins K1, K2 and K3 are available, e.g., from Sigma-Aldrich.

The lipophilic component is provided in the formulation in an amount sufficient to enhance the skin penetration of the vitamin K analog. In certain embodiments, the formulation comprises from about 1 to about 100% of a lipophilic component or a combination of lipophilic components. In other embodiments, the formulation comprises from about 1% to about 35% (w/w), from about 3% to about 15% (w/w), or from about 6% to 12% (w/w) of the lipophilic component. In other embodiments, the formulation comprises about 3% (w/w), about 5% (w/w), about 6% (w/w), about 10% (w/w), about 12% (w/w) or about 15% (w/w) of the lipophilic component.

Lipophilic components that may be used in the topical formulation of the invention are commercially available and include, but are not limited to, polycarbons, e.g., mineral oils and emulsifying wax; petrolatum, synthetic oils, e.g., isopropyl myristate, diethyl sebacate, diisopropyl adipate, caprylic/capric triglyceride; octyldodecyl, isostearyl isostearate, decyl oleate, isopropyl palmitate; and silicone oils, e.g., cyclopentasiloxane, cyclohexasiloxane, cyclotetrasiloxane, dimethicone; vegetable oils, e.g., linseed oil, tung oil, castor oil, peanut oil, olive oil, almond oil; or combinations thereof. In a preferred embodiment, the lipophilic component is selected from the group consisting of isopropyl myristate, diethyl sebacate, diisoproyl adipate, caprylic/capric triglyceride and combinations thereof.

The topical formulation of the invention further comprises one or more gelling agents, typically at a concentration from about 0.1 to 5% (w/w). The term "gelling agent" as used herein, is a substance which thickens and modifies the viscosity of a liquid vehicle to provide ease and uniformity of application. In some cases, high molecular weight gelling agents may control the rate of skin absorption of the drug by a type of controlled release process. In addition, gelling agents may act as emulsion formers and emulsion stabilizers, e.g., as dispersing agents (i.e., to improve the separation of particles and to prevent settling or clumping).

Pharmaceutically acceptable gelling agents employed in the topical formulation of the invention are commercially available and include, but are not limited to, starch, cellulose derivatives, acrylic derivatives, magnesium-aluminum silicates, xanthan gum and colloidal silica, or combinations thereof.

In some embodiments, the gelling agent is a cellulose derivative, such as, methylcelluloses (Methocel, Metolose), ethylcelluloses (Ethocel, Aquacoat®), hydroxypropylmethylcelluloses (Kenal, Methocel, Hypromelose), hydroxyethylcelluloses (Cellosize, Natrosol), hydroxypropylcelluloses (Klucel), carboxymethylcelluloses, cross-linked or not, in sodium or calcium form (Akucell, Nymcel, Tylose CB, Croscarmellose, Acdisol) or combinations thereof.

In other embodiments, the gelling agent is an acrylic derivative, e.g., a carbomer or acrylic based polymer. In preferred embodiments, the acrylic based polymer is a Carbopol® polymer, e.g., Carbopol® 71G, Carbopol® 971P NF, Carbopol® 980 NF, Carbopol® 981 NF and Carbopol® 941 NF. In certain embodiments, the acrylic based polymer is a Pemulen® polymeric emulsifier, e.g., Pemulen® TR-1 NF or Pemulen® TR-2 NF, or combinations thereof. In one preferred embodiment, the gelling agent is a combination of Carbopol® 981 NF and Pemulen® TR-1 NF.

The topical formulation of the invention further comprises water, preferably purified, to act as a carrier to yield a formulation that is cosmetically acceptable and moisturizing. Typically, the formulation comprises from about 30 to 95% (w/w) water or about 60 to 90% (w/w) water.

In further embodiments, a neutralizer or buffer may be added to stabilize the pH of the formulation to increase the viscosity to an acceptable level. Examples of neutralizing agents include, but are not limited to, sodium hydroxide, potassium hydroxide and triethanolamine. In related embodiments, sufficient neutralizer is added to the formulation to maintain a pH of about 4.0 to 8.0, from about 5.0 to 6.5, or from about 5.0 to 6.0. In another embodiment, sufficient neutralizer is added to maintain a pH of about 5.5.

In other embodiments, a preservative may be included in the formulation of the present invention to prevent microorganism overgrowth with time. In certain embodiments, the preservative is present in the formulation in a w/w amount of from about 0.01 to about 50%, preferably in an amount of from 0.01 to 5%, more preferably in an amount from about 0.5% to 5%. In one embodiment, the formulation contains about 1% (w/w) of the preservative.

Any preservative known to those skilled in the art and not otherwise deleterious to the formulation may be used. Examples of suitable preservatives that include, but are not limited to, alkyl alcohols (e.g., benzyl alcohol); parabens, (e.g., butyl paraben, propyl paraben) their salts and esters; benzoic acid, its salts and its esters; sorbic acid and its salts; triclosan; imidazolidinyl urea; phenoxyethanol; DMDM hydantoin; diazolidinyl urea and chlorphenesin butylated hydroxytoluene, disodium dedtate, citric acid; or combinations thereof. In one preferred embodiment, the preservative included in the formulation is benzyl alcohol.

Additional components that may be included in the topical formulations of the invention include UVA and UVB filters such as benzophenone-3, butyl methoxydibenzoyl methane, octocrylene, octyl methoxycinnamate, 4-methylbenzylidene camphor, octyl salicylate, terephthalylidene dicamphor sulfanic acid and drometrizole trisiloxane; colorants such as lipophilic colorants, hydrophilic colorants, pigments and mother-of-pearl conventionally used in cosmetic or dermatological compositions, topical anesthetics (e.g., benzocaine, butamben, dibucaine, lidocaine, oxybuprocaine, pramoxine, proparacaine, proxymetacaine, and tetracaine), polyol prepolymers (e.g., a degradable biocompatible material, e.g., artificial skin), and phospholipids, and their mixtures.

II. Packaging

The topical formulation of the invention may be conveniently packaged using any light impermeable commercial container (e.g., dark glass, plastic or aluminum) suitable for topical administration including, but not limited to, cans with spray pumps, bottles, jars, vials, tubes and single use packets, which are capable of maintaining the chemical stability of the active ingredient, a vitamin K analog, for at least 12 months at 25° C. or at refrigeration (at 4° C.). The containers can also be provided with a cap and means for dispensing the topical formulation, e.g., a pump or applicator.

In certain embodiments, the container is a compressible, e.g., can be readily compressed to extrude the topical formulation by an individual with average strength, including but not limited to flexible plastic and aluminum tubes, and flexible unit-dose foil pouches. In one preferred embodiment, the container is an aluminum tube, more preferably, with an internal protective coating (e.g., a lacquer coating) as described in the following Examples.

Typically, the pharmaceutical formulation of the invention is provided in a container having a capacity from about 10-150 g, 20-120, 10 to 200 g or from about 20 to 150 g. In one embodiment, the pharmaceutical formulation is provided in an aluminum tube having a 30 g capacity. In a preferred embodiment, the pharmaceutical formulation is provided in an aluminum tube having a 100 g capacity.

III. Methods of Treatment and/or Prevention

The invention further provides methods of treating a dermatological condition comprising administering to a patient a therapeutically effective amount of the topical formulation described herein.

The term "treating" as used herein, unless otherwise indicated, means reversing, alleviating, inhibiting the progress of, or preventing, either partially or completely, one or more conditions or symptoms associated with a dermatological condition. The term "treatment" as used herein, unless otherwise indicated, refers to the act of treating as "treating" is defined immediately above.

Similarly, the phrase "therapeutically effective amount" refers to the amount of the topical formulation of the invention capable of treating the dermatological condition. The dose and frequency of administration will depend on the type and severity of the dermatological condition being treated and the size of the affected area. A therapeutically effective amount of the formulation can be administered in single or multiple doses over a period of days, weeks or months as needed to treat the condition. The dose and frequency of administration can also be adjusted up or down by the prescribing physician depending on the degree of responsiveness to the treatment by the particular patient. Typically, the topical formulation of the invention is administered at least once a day and in one embodiment, the formulation is administered between one and four timer per day.

The term "dermatological condition" as used herein refers to diseases or disorders associated with inflammation of the skin (e.g., epidermis or dermis) including, but not limited to, rashes, eczema, psoriasis, dermatitis, keratosis, acne and epithelial toxicity caused by administration to a patient of a dose (single or divided) or series of doses (e.g., a course of treatment) of an EGFR inhibitor useful in treating cancer.

As used herein, the term "epithelial toxicity" refers to an abnormality or dysfunction of the epithelium manifested in a patient receiving anti-EGFR therapy by one or more symptoms or conditions including, but not limited to skin rash, e.g., macular, papular, pustular rash, commonly referred to as acne-like rash (or folliculitis); seborrheic dermatitis-like rash; xerosis; fissures; telangiectasia; hyperpigmentation; hair atrophy or loss; hair follicle dysplasia; interfollicular epidermal hyperplasia; diffuse erythema with follicular papulopustules; oedematous facial erythema; periungual (the area that surrounds the nail) alterations; and a failure to heal or a delayed healing after injury.

As used herein, the term "patient" or "subject" preferably refers to a human suffering from or at risk of suffering from a dermatological complaint. However, the term "patient" can also refer to non-human animals, preferably mammals such as dogs, cats, horses, cows, pigs, sheep and non-human primates, among others. Preferably, the patient is a human that is being treated or has received treatment with an EGFR inhibitor.

As used interchangeably herein, the terms "EGFR inhibitor" and "anti-EGFR therapy" refer to any EGFR inhibitor that is currently known in the art or that will be identified in the future, and includes any chemical entity that, upon administration to a patient, results in inhibition of a biological activity associated with activation of the EGFRs in the patient, including any of the downstream biological effects otherwise resulting from the binding to an EGFR of its natural ligand. Such EGFR inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor or a portion thereof, thereby making the receptor inaccessible to its natural ligand so that normal biological activity is prevented or reduced. EGFR inhibitors include but are not limited to low molecular weight inhibitors, antibodies or antibody fragments, antisense constructs and ribozymes.

Examples of EGFR inhibitors include but are not limited to those classified in the art as quinazoline EGFR inhibitors, pyrido-pyrimidine EGFR inhibitors, pyrimido-pyrimidine EGFR inhibitors, pyrrolo-pyrimidine EGFR inhibitors, pyrazolo-pyrimidine EGFR inhibitors, phenylamino-pyrimidine EGFR inhibitors, oxindole EGFR inhibitors, indolocarbazole EGFR inhibitors, phthalazine EGFR inhibitors, isoflavone EGFR inhibitors, quinalone EGFR inhibitors, and tyrphostin EGFR inhibitors.

Non-limiting examples of low molecular weight EGFR include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of low molecular weight EGFR inhibitors include any of the EGFR inhibitors described in Traxler, P., 1998, Exp. Opin. Ther. Patents 8(12):1599-1625.

Specific preferred examples of low molecular weight EGFR inhibitors include [6,7-bis(2-methoxyethoxy)-4-quinazolin-4-yl]-(3-ethynylphenyl)amine (U.S. Pat. No. 5,747,498 issued May 5, 1998 and Moyer et al., 1997, supra); C1-1033 and PD183805 (Sherwood et al., 1999, Proc. Am. Assoc. Cancer Res. 40:723); and ZD1839 (Woodburn et al., 1997, Proc. Am. Assoc. Cancer Res. 38:633).

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

In additional embodiments, the active compounds of the invention can be co-administered with other agents. For example, additional treatments include oral or topical anti-inflammatory or antibiotic medications, sunscreens (e.g., UV-A and UV-B filtering agents), analgesic agents active topically, and the like. The additional agents can be administered either as part of the topical formulation or in a separate pharmaceutical composition. The additional agents can be administered prior to, at the same time, or subsequent to administration of the topical formulation of the invention.

This invention is further illustrated by the following examples which should not be construed as limiting. The contents of all references, patents and published patent applications cited throughout this application are hereby incorporated by reference.

EXAMPLE 1

Menadione Solubility

This study focused on evaluating the solubility properties of menadione in hydrophilic and lipophilic excipients used in topical pharmaceutical products. Initially, solubility studies were conducted in single solvents. The solubility of menadione in the selected solvents is presented in Table 1.

TABLE 1

Estimated Solubility of Menadione in Single Solvents

| Lab Reference | Solvent | (% w/w) |
|---|---|---|
| 2368-3A | Benzyl Alcohol | Greater than 10% |
| 2368-5A | Dimethyl Isosorbide | Greater than 10% |
| 2368-4A | Diethyl Sebacate | 8 to 10% |
| 2368-5B | Diethylene Glycol Monoethylether (Transcutol) | 5 to 7% |
| 2368-3B | Caprylic/Capric Triglyceride | 4 to 5% |
| 2368-4B | Diisopropyl Adipate | 4 to 5% |
| 2368-11B | Ethyl Alcohol (200 proof) | 2 to 4% |
| 2368-24A | Polyethylene Glycol 200 | 2 to 4% |
| 2368-25A | Polyethylene Glycol 400 | Greater than 2% |
| 2368-6A | Isopropyl Myristate | 2 to 3% |
| 2368-7A | Oleic Acid | 2 to 3% |
| 2368-7B | Oleyl Alcohol | 2 to 3% |
| 2368-9B | PPG-3 Myristyl Ether | 2 to 3% |
| 2368-8A | Peanut Oil | 1.5 to 2% |
| 2368-10B | Isopropyl Alcohol | 1 to 2% |
| 2368-6B | Octyl Dodecanol | 1 to 2% |
| 2368-8B | Propylene Glycol | Less than 1% |
| 2368-42A | Mineral Oil | Less than 0.1% |
| 2368-9A | Purified Water | Less than 0.04% |

Based on the single solvent solubility data, a menadione compatibility study with selected solvents was conducted. Solutions containing 1% w/w of menadione were prepared, packaged in borosilicate clear glass vials, wrapped in aluminum foil and stored at 5° C. (dark), 25° C. (dark), and 40° C. (dark) for a period of 1 month. The physico-chemical properties of the 1% menadione single solvent solutions are presented in: Table 2.

TABLE 2

Menadione Compatibility with Single Solvent Systems

| Solvent System | Pull Point | Condition | Description | Assay by HPLC |
|---|---|---|---|---|
| 1% Menadione in Benzyl Alcohol | $T_0$ | Initial | Clear yellow solution | N.T |
| | 1 Month | 5° C./dark | Conforms | 0.97 |
| | | 25° C./dark | Conforms | 0.97 |
| | | 40° C./dark | Conforms | 0.97 |
| 1% Menadione in Caprilyc/Capric Triglyceride | $T_0$ | Initial | Clear yellow solution | N.T |
| | 1 Month | 5° C./dark | Conforms | 0.97 |
| | | 25° C./dark | Conforms | 0.98 |
| | | 40° C./dark | Conforms | 0.98 |
| 1% Menadione in Diethyl Sebacate | $T_0$ | Initial | Clear yellow solution | N.T |
| | 1 Month | 5° C./dark | Conforms | 1.00 |
| | | 25° C./dark | Conforms | 1.01 |
| | | 40° C./dark | Conforms | 1.00 |
| 1% Menadione in Diisopropyl Adipate | $T_0$ | Initial | Clear yellow solution | N.T |
| | 1 Month | 5° C./dark | Conforms | 0.98 |
| | | 25° C./dark | Conforms | 0.98 |
| | | 40° C./dark | Conforms | 0.98 |

TABLE 2-continued

Menadione Compatibility with Single Solvent Systems

| Solvent System | Pull Point | Condition | Description | Assay by HPLC |
|---|---|---|---|---|
| 1% Menadione in Dimethyl Isosorbide | $T_0$ 1 Month | Initial 5° C./dark 25° C./dark 40° C./dark | Clear yellow solution Deepening in Color Deepening in Color Brownish solution | N.T N.T N.T N.T |
| 1% Menadione in Transcutol | $T_0$ 1 Month | Initial 5° C./dark 25° C./dark 40° C./dark | Clear yellow solution Deepening in Color Deepening in Color Brownish solution | N.T N.T N.T N.T |
| 1% Menadione in Isopropyl Myristate | $T_0$ 1 Month | Initial 5° C./dark 25° C./dark 40° C./dark | Clear yellow solution Conforms Conforms Conforms | N.T 1.00 1.00 1.00 |
| 1% Menadione in Polyethylene Glycol 400 | $T_0$ 1 Month | Initial 5° C./dark 25° C./dark 40° C./dark | Clear yellow solution Brown solution Brown/orange solution Red solution | N.T N.T N.T N.T |

N.T = Not Tested

As shown in Table 2, menadione was deemed compatible with the selected solvents (i.e. caprylic/capric triglyceride, diethyl sebacate, diisopropyl adipate, and isopropyl myristate) as demonstrated by the solutions retaining their physical appearance and their chemical potency assessed by HPLC after one (1) month of storage at 5° C. (dark), 25° C. (dark), and 40° C. (dark). In contrast, dimethyl isosorbide, transcutol and polyethylene glycol 400 showed signs of incompatibility with menadione as discoloration of the tested solutions were reported in all of the conditions evaluated.

EXAMPLE 2

Formulation Development

The objective during formulation development was to develop a topical formulation with the following properties:
If possible, a formulation not containing Ethyl Alcohol
If possible, compendial formulation components
Vehicle composed of excipients present in topical products previously approved by FDA, as demonstrated by the excipient being listed on FDA's Inactive Ingredient Guide
Chemically stable
Physically stable
Highly spreadable and cosmetically elegant
Pharmaceutically acceptable attributes
Well preserved product
Delivers a target Epidermal Menadione Concentration: 0.1-0.5 mM Formulation Prototypes Based on the objective of delivering a concentration of 0.1-0.5 mM menadione to the epidermal layers, and with the assumption that approximately 2 to 10% of the product's applied dose reaches the target area, a target drug concentration of 0.2% w/w in the formulation was selected (0.2% is equal to approximately 12 mM, therefore the estimated epidermal delivery of 2-10% would be equal to an epidermal concentration of approximately 0.2-1.2 mM).

Formulations with the target drug concentration of 0.2% w/w, were initially developed and various forms were examined. The investigation consisted of evaluating aqueous emulsions and non-aqueous formulations. Formulations with different emulsifying agents and preservatives were also examined.

The compositions of prototype formulations are presented in Table 3.

TABLE 3

Composition of Menadione Prototype Formulations

| Ingredients | % w/w | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Menadione, USP | 0.2 | 0.2 | 0.2 | 0.2 | 0.2 | 0.2 | 0.2 | 0.2 | 0.2 | 0.4 | 0.2 | 0.2 |
| Diethyl Sebacate | 3.0 | — | — | — | — | 10.0 | 10.0 | 10.0 | 10.0 | 10.0 | 15.0 | 15.0 |
| Diisopropyl Adipate | — | 6.0 | — | — | — | — | — | — | — | — | — | — |
| Isopropyl Myristate, NF | — | — | 12.0 | 12.0 | 12.0 | — | — | — | — | — | 50.0 | 10.0 |
| White Petrolatum, USP | — | — | — | — | — | 5.0 | 5.0 | 5.0 | — | 5.0 | — | — |
| Light Mineral Oil, NF | — | — | — | — | — | — | — | — | — | — | 34.8 | 64.8 |
| Cyclomethicone 5-NF | — | — | — | — | — | — | — | — | — | — | — | 10.0 |
| Brij 72 | — | — | — | — | — | 3.5 | 3.5 | — | 3.5 | 3.5 | — | — |
| Brij 721 | — | — | — | — | — | 1.5 | 1.5 | — | 1.5 | 1.5 | — | — |
| Emulsifying Wax | — | — | — | — | — | — | — | 12.0 | — | — | — | — |
| Pemulen TR-1, NF | 0.3 | 0.3 | 0.3 | 0.3 | 0.3 | — | — | — | — | — | — | — |
| Carbopol 981, NF | 0.1 | 0.1 | 0.1 | 0.1 | 0.1 | 0.1 | 0.1 | — | — | — | — | — |
| Methylparaben, NF | 0.17 | 0.17 | 0.17 | — | — | — | 0.17 | 0.17 | 0.17 | 0.17 | — | — |
| Propylparaben, NF | 0.03 | 0.03 | 0.03 | — | — | — | 0.03 | 0.03 | 0.03 | 0.03 | — | — |
| Benzyl Alcohol, NF | — | — | — | 1.0 | 1.0 | 1.0 | — | — | — | — | — | — |

TABLE 3-continued

Composition of Menadione Prototype Formulations

| Ingredients | 1 | 2 | 3 | 4 | 5 | 6 | 7 | 8 | 9 | 10 | 11 | 12 |
|---|---|---|---|---|---|---|---|---|---|---|---|---|
| Propylene Glycol, USP | — | — | — | — | 5.0 | — | — | — | — | — | — | — |
| 4% NaOH Solution | — | — | q.s. pH 5.0-6.0 | — | — | — | — | — | — | — | — | — |
| Sodium Phosphate Monobasic | — | — | — | — | — | — | — | q.s. pH 5.0-6.0 | — | — | — | — |
| Sodium Phosphate Dibasic | — | — | — | — | — | — | — | q.s. pH 5.0-6.0 | — | — | — | — |
| Purified Water | — | — | — | — | — | q.s. ad 100 | — | — | — | — | — | — |

The prototype formulations were compounded under yellow light and packaged in borosilicate clear glass vials. Vials designated to be protected from light were wrapped with aluminum foil. All vials were stored at 5° C. (dark), 25° C. (dark), 25° C. (ambient light) and 40° C. (dark) for a period of up to 6 months to assess the stability of these formulation prototypes. Each formulation also underwent a freeze thaw study for 1 month (approximately 4 cycles per month between −20° C. and ambient room temperature) after which each formulation was visually inspected.

The physical and chemical stability results for each prototype formulation are shown in Table 4 to Table 15.

TABLE 4

Physical & Chemical Stability of Prototype 1

| Prototype 1 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.4 | 3,800 | 101.4 |
| t = 1 mo | Conforms | N.T | N.T | N.T |
| Interval | 5° C. dark | | | |
| t = 0 mo | Light yellowish lotion | 5.4 | 3,800 | 101.4 |
| t = 1 mo | Conforms | 5.5 | 3,600 | 103.0 |
| t = 3 mo | Conforms | 5.4 | 3,800 | 101.0 |
| t = 6 mo | Conforms | 5.3 | 3700 | 98.8 |
| Interval | 25° C. Ambient Light | | | |
| t = 0 mo | Light yellowish lotion | 5.2 | 3,800 | 98.8 |
| t = 1 mo | Color Deepening/Phase Separation | N.T | N.T | N.T |
| Interval | 25° C. dark | | | |
| t = 0 mo | Light yellowish lotion | 5.2 | 3,800 | 98.8 |
| t = 1 mo | Conforms | 5.4 | 3,500 | 104.5 |
| t = 3 mo | Conforms | 5.4 | 3,600 | 101.6 |
| t = 6 mo | Does not conform[2] | 5.4 | 3,500 | 98.5 |
| Interval | 40° C. dark | | | |
| t = 0 mo | Light yellowish lotion | 5.2 | 3,800 | 98.8 |
| t = 1 mo | Conforms | 5.4 | 3,500 | 105.7 |
| t = 3 mo | Color Deepening | 5.4 | 2,800 | 99.8 |
| t = 6 mo | Does not conform[2] | N.T | 2,100 | 96.2 |

N.T = Not Tested
[1]Viscosity Parameters: Spindle 27, Speed 30 rpm
[2]Large, dark oil droplets observed

TABLE 5

Physical & Chemical Stability of Prototype 2

| Prototype 2 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.5 | 3,600 | 100.5 |
| t = 1 mo | Conforms | N.T | N.T | N.T |
| Interval | 5° C. dark | | | |
| t = 0 mo | Light yellowish lotion | 5.5 | 3,600 | 100.5 |
| t = 1 mo | Conforms | 5.5 | 3,300 | 100.7 |
| t = 3 mo | Conforms | 5.5 | 3,500 | 99.4 |
| Interval | 25° C. Ambient Light | | | |
| t = 0 mo | Light yellowish lotion | 5.5 | 3,600 | 100.5 |
| t = 1 mo | Color Deepening/Phase Separation | N.T | N.T | N.T |
| Interval | 25° C. dark | | | |
| t = 0 mo | Light yellowish lotion | 5.5 | 3,600 | 100.5 |
| t = 1 mo | Conforms | 5.5 | 3,300 | 101.2 |
| t = 3 mo | Conforms | 5.5 | 3,300 | 98.0 |
| Interval | 40° C. dark | | | |
| t = 0 mo | Light yellowish lotion | 5.5 | 3,600 | 100.5 |
| t = 1 mo | Conforms | 5.5 | 3,000 | 100.2 |
| t = 3 mo | Color Deepening | 5.5 | 2,700 | 96.3 |

N.T = Not Tested
[1]Viscosity Parameters: Spindle 27, Speed 30 rpm

TABLE 6

Physical & Chemical Stability of Prototype 3

| Prototype 3 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.5 | 4,200 | 101.6 |
| t = 1 mo | Conforms | N.T | N.T | N.T |
| Interval | 5° C. dark | | | |
| t = 0 mo | Light yellowish lotion | 5.5 | 4,200 | 101.6 |
| t = 1 mo | Conforms | 5.4 | 3,800 | 99.3 |
| t = 3 mo | Conforms | 5.5 | 4,100 | 97.9 |

TABLE 6-continued

Physical & Chemical Stability of Prototype 3

| Prototype 3 | Appearance | pH (neat) | Viscosity (cps)[1] | Assay by HPLC (% of LC) |
|---|---|---|---|---|
| Interval | 25° C. Ambient Light | | | |
| t = 0 mo | Light yellowish lotion | 5.5 | 4,200 | 101.6 |
| t = 1 mo | Color Deepening/Phase Separation | N.T | N.T | N.T |
| Interval | 25° C. dark | | | |
| t = 0 mo | Light yellowish lotion | 5.5 | 4,200 | 101.6 |
| t = 1 mo | Conforms | 5.4 | 3,800 | 100.8 |
| t = 3 mo | Conforms | 5.5 | 4,000 | 97.7 |
| Interval | 40° C. dark | | | |
| t = 0 mo | Light yellowish lotion | 5.5 | 4,200 | 101.6 |
| t = 1 mo | Conforms | 5.4 | 3,900 | 98.7 |
| t = 3 mo | Color Deepening | 5.5 | 3,200 | 97.7 |

N.T = Not Tested
[1] Viscosity Parameters: Spindle 27, Speed 30 rpm

TABLE 7

Physical & Chemical Stability of Prototype 4

| Prototype 4 | Appearance | pH (neat) | Viscosity (cps)[1] | Assay by HPLC (% of LC) |
|---|---|---|---|---|
| Interval | Freeze/Thaw | | | |
| t = 0 mo | Yellow lotion | 5.2 | 3,800 | 98.8 |
| t = 1 mo | Conforms | N.T | N.T | N.T |
| Interval | 5° C. dark | | | |
| t = 0 mo | Yellow lotion | 5.2 | 3,800 | 98.8 |
| t = 1 mo | Conforms | 5.4 | 3,100 | 98.2 |
| t = 3 mo | Conforms | 5.5 | 3,600 | 98.1 |
| t = 6 mo | Conforms | 5.4 | 3,600 | 96.1 |
| Interval | 25° C. Ambient Light | | | |
| t = 0 mo | Yellow lotion | 5.2 | 3,800 | 98.8 |
| t = 1 mo | Heterogeneous | N.T | N.T | N.T |
| Interval | 25° C. dark | | | |
| t = 0 mo | Yellow lotion | 5.2 | 3,800 | 98.8 |
| t = 1 mo | Conforms | 5.4 | 3,000 | 99.5 |
| t = 3 mo | Conforms | 5.5 | 3,400 | 96.5 |
| t = 6 mo | Conforms | 5.4 | 3,300 | 95.6 |
| Interval | 40° C. dark | | | |
| t = 0 mo | Yellow lotion | 5.2 | 3,800 | 98.8 |
| t = 1 mo | Slight color deepening | 5.4 | 2,600 | 97.1 |
| t = 3 mo | Thin, deepening in color | 5.5 | 2,500 | 96.4 |
| t = 6 mo | Thin, deepening in color | 5.4 | 1,800 | 94.7 |

N.T = Not Tested
[1] Viscosity Parameters: Spindle 27, Speed 30 rpm

TABLE 8

Physical & Chemical Stability of Prototype 5

| Prototype 5 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.6 | 3,900 | 101.5 |
| t = 1 mo | Conforms | N.T | N.T | N.T |
| Interval | 5° C. dark | | | |
| t = 0 mo | Light yellowish lotion | 5.6 | 3,900 | 101.5 |
| t = 1 mo | Conforms | 5.6 | 3,100 | 98.5 |
| t = 3 mo | Conforms | 5.6 | 3,900 | 96.8 |
| Interval | 25° C. Ambient Light | | | |
| t = 0 mo | Light yellowish lotion | 5.6 | 3,900 | 101.5 |
| t = 1 mo | Color Deepening/Phase Separation | N.T | N.T | N.T |
| Interval | 25° C. dark | | | |
| t = 0 mo | Light yellowish lotion | 5.6 | 3,900 | 101.5 |
| t = 1 mo | Conforms | 5.6 | 3,000 | 99.2 |
| t = 3 mo | Conforms | 5.6 | 3,700 | 95.7 |
| Interval | 40° C. dark | | | |
| t = 0 mo | Light yellowish lotion | 5.6 | 3,900 | 101.5 |
| t = 1 mo | Slight color deepening | 5.6 | 3,100 | 96.8 |
| t = 3 mo | Thin, deepening in color | 5.6 | 3,100 | 84.1 |

N.T = Not Tested
[1] Viscosity Parameters: Spindle 27, Speed 30 rpm

TABLE 9

Physical & Chemical Stability of Prototype 6

| Prototype 6 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 6.0 | 460 | 100.9 |
| t = 1 mo | Conforms | N.T | N.T | N.T |
| Interval | 5° C. dark | | | |
| t = 0 mo | Light yellowish lotion | 6.0 | 460 | 100.9 |
| t = 1 mo | Conforms | 6.4 | 390 | 95.1 |
| t = 3 mo | Conforms | 6.1 | 580 | 98.5 |
| Interval | 25° C. Ambient Light | | | |
| t = 0 mo | Light yellowish lotion | 6.0 | 460 | 100.9 |
| t = 1 mo | Color Deepening/Phase Separation | N.T | N.T | N.T |
| Interval | 25° C. dark | | | |
| t = 0 mo | Light yellowish lotion | 6.0 | 460 | 100.9 |
| t = 1 mo | Conforms | 6.2 | 450 | 98.1 |
| t = 3 mo | Conforms | 6.1 | 440 | 98.0 |
| Interval | 40° C. dark | | | |
| t = 0 mo | Light yellowish lotion | 6.0 | 460 | 100.9 |
| t = 1 mo | Conforms | 6.3 | 360 | 95.9 |
| t = 3 mo | Phase Separation | N.T | N.T | N.T |

N.T = Not Tested
[1] Viscosity Parameters: Spindle 21, Speed 60 rpm

TABLE 10

Physical & Chemical Stability of Prototype 7

| Prototype 7 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.8 | 390 | 103.0 |
| t = 1 mo | Conforms | N.T | N.T | N.T |
| Interval | 5° C. dark | | | |
| t = 0 mo | Light yellowish lotion | 5.8 | 390 | 103.0 |
| t = 1 mo | Conforms | 5.9 | 450 | 99.8 |
| t = 3 mo | N.T | N.T | N.T | N.T |
| Interval | 25° C. Ambient Light | | | |
| t = 0 mo | Light yellowish lotion | 5.8 | 390 | 103.0 |
| t = 1 mo | Phase Separation | N.T | N.T | N.T |
| t = 3 mo | N.T | N.T | N.T | N.T |
| Interval | 25° C. dark | | | |
| t = 0 mo | Light yellowish lotion | 5.8 | 390 | 103.0 |
| t = 1 mo | Conforms | 5.9 | 450 | 100.6 |
| t = 3 mo | N.T | N.T | N.T | N.T |
| Interval | 40° C. dark | | | |
| t = 0 mo | Light yellowish lotion | 5.8 | 390 | 103.0 |
| t = 1 mo | Phase Separation | N.T | N.T | N.T |
| t = 3 mo | N.T | N.T | N.T | N.T |

N.T = Not Tested
[1]Viscosity Parameters: Spindle 21, Speed 60 rpm

TABLE 11

Physical & Chemical Stability of Prototype 8

| Prototype 8 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.9 | 12,200 | 102.1 |
| t = 1 mo | Conforms | N.T | N.T | N.T |
| Interval | 5° C. dark | | | |
| t = 0 mo | Light yellowish lotion | 5.9 | 12,200 | 102.1 |
| t = 1 mo | Conforms | 5.9 | 12,200 | 92.9 |
| t = 3 mo | Conforms | 5.9 | 12,200 | 102.8 |
| Interval | 25° C. Ambient Light | | | |
| t = 0 mo | Light yellowish lotion | 5.9 | 12,200 | 102.1 |
| t = 1 mo | Color deepening | N.T | N.T | N.T |
| Interval | 25° C. dark | | | |
| t = 0 mo | Light yellowish lotion | 5.9 | 12,200 | 102.1 |
| t = 1 mo | Conforms | 5.9 | 12,200 | 103.2 |
| t = 3 mo | Conforms | 5.8 | 12,200 | 101.2 |
| Interval | 40° C. dark | | | |
| t = 0 mo | Light yellowish lotion | 5.9 | 12,200 | 102.1 |
| t = 1 mo | Conforms | 5.8 | 4,000 | 98.2 |
| t = 3 mo | Slight color change | 5.6 | 8,600 | 102.8 |

N.T = Not Tested
[1]Viscosity Parameters: Spindle 14, Speed 60 rpm

TABLE 12

Physical & Chemical Stability of Prototype 9

| Prototype 9 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.8 | 320 | 105.7 |
| t = 1 mo | Conforms | N.T | N.T | N.T |
| Interval | 5° C. dark | | | |
| t = 0 mo | Light yellowish lotion | 5.8 | 320 | 105.7 |
| t = 1 mo | Conforms | 5.9 | 360 | 103.8 |
| t = 3 mo | N.T | N.T | N.T | N.T |
| Interval | 25° C. Ambient Light | | | |
| t = 0 mo | Light yellowish lotion | 5.8 | 320 | 105.7 |
| t = 1 mo | Phase Separation | N.T | N.T | N.T |
| Interval | 25° C. dark | | | |
| t = 0 mo | Light yellowish lotion | 5.8 | 320 | 105.7 |
| t = 1 mo | Conforms | 5.8 | 410 | 102.8 |
| t = 3 mo | N.T | N.T | N.T | N.T |
| Interval | 40° C. dark | | | |
| t = 0 mo | Light yellowish lotion | 5.8 | 320 | 105.7 |
| t = 1 mo | Phase Separation | N.T | N.T | N.T |
| t = 3 mo | N.T | N.T | N.T | N.T |

N.T = Not Tested
[1]Viscosity Parameters: Spindle 21, Speed 60 rpm

TABLE 13

Physical & Chemical Stability of Prototype 10

| Prototype 10 | Appearance | pH (neat) | Viscosity (cps)[1] | Assay by HPLC (% of LC) |
|---|---|---|---|---|
| Interval | Freeze/Thaw | | | |
| t = 0 mo | Light yellowish lotion | 5.8 | 350 | 100.5 |
| t = 1 mo | Conforms | N.T | N.T | N.T |
| Interval | 5° C. dark | | | |
| t = 0 mo | Light yellowish lotion | 5.8 | 350 | 100.5 |
| t = 1 mo | Conforms | 5.8 | 360 | 93.3 |
| t = 3 mo | N.T | N.T | N.T | N.T |
| Interval | 25° C. Ambient Light | | | |
| t = 0 mo | Light yellowish lotion | 5.8 | 350 | 100.5 |
| t = 1 mo | Phase Separation | N.T | N.T | N.T |
| Interval | 25° C. dark | | | |
| t = 0 mo | Light yellowish lotion | 5.8 | 350 | 100.5 |
| t = 1 mo | Conforms | 5.8 | 340 | 99.9 |
| t = 3 mo | N.T | N.T | N.T | N.T |
| Interval | 40° C. dark | | | |
| t = 0 mo | Light yellowish lotion | 5.8 | 350 | 100.5 |
| t = 1 mo | Phase Separation | N.T | N.T | N.T |
| t = 3 mo | N.T | N.T | N.T | N.T |

N.T = Not Tested
[1]Viscosity Parameters: Spindle 21, Speed 60 rpm

TABLE 14

Physical & Chemical Stability of Prototype 11

| Prototype 11 | Appearance | pH (neat) | Viscosity (cps)[1] | Assay by HPLC (% of LC) |
|---|---|---|---|---|
| Interval | Freeze/Thaw | | | |
| t = 0 mo | Yellow Solution | N/A | N/A | 98.3 |
| t = 1 mo | Conforms | N.T | N.T | N.T |
| Interval | 5° C. dark | | | |
| t = 0 mo | Yellow Solution | N/A | N/A | 98.3 |
| t = 1 mo | Conforms | N/A | N/A | 98.0 |
| t = 3 mo | Conforms | N/A | N/A | N.T |
| Interval | 25° C. Ambient Light | | | |
| t = 0 mo | Yellow Solution | N/A | N/A | 98.3 |
| t = 1 mo | Color change | N.T | N.T | 15.1 |
| Interval | 25° C. dark | | | |
| t = 0 mo | Yellow Solution | N/A | N/A | 98.3 |
| t = 1 mo | Conforms | N/A | N/A | 98.9 |
| t = 3 mo | Conforms | N/A | N/A | N.T |
| Interval | 40° C. dark | | | |
| t = 0 mo | Yellow Solution | N/A | N/A | 98.3 |
| t = 1 mo | Conforms | N/A | N/A | 99.5 |
| t = 3 mo | Conforms | N/A | N/A | N.T |

N.T = Not Tested
[1]Viscosity Parameters: Spindle 27, Speed 30 rpm

TABLE 15

Physical & Chemical Stability of Prototype 12

| Prototype 12 | Appearance | pH (neat) | Viscosity (cps)[1] | Assay by HPLC (% of LC) |
|---|---|---|---|---|
| Interval | Freeze/Thaw | | | |
| t = 0 mo | Yellow Solution | N/A | N/A | 98.6 |
| t = 1 mo | Conforms | N.T | N.T | N.T |
| Interval | 5° C. dark | | | |
| t = 0 mo | Yellow Solution | N/A | N/A | 98.6 |
| t = 1 mo | Conforms | N/A | N/A | 99.0 |
| t = 3 mo | Conforms | N/A | N/A | N.T |
| Interval | 25° C. Ambient Light | | | |
| t = 0 mo | Yellow Solution | N/A | N/A | 98.6 |
| t = 1 mo | Color change | N.T | N.T | 10.6 |
| Interval | 25° C. dark | | | |
| t = 0 mo | Yellow Solution | N/A | N/A | 98.6 |
| t = 1 mo | Conforms | N/A | N/A | 98.7 |
| t = 3 mo | Conforms | N/A | N/A | N.T |
| Interval | 40° C. dark | | | |
| t = 0 mo | Yellow Solution | N/A | N/A | 98.6 |
| t = 1 mo | Conforms | N/A | N/A | 98.3 |
| t = 3 mo | Conforms | N/A | N/A | N.T |

N.T = Not Tested
[1]Viscosity Parameters: Spindle 21, Speed 60 rpm

All the compositions presented in Table 3 showed a discoloration and/or a deterioration of the system when stored unprotected at ambient light conditions. These results indicate that the photodegradation of menadione may have a deleterious effect of unknown mechanism on the physical properties of the lotion. For this reason a container-closure system that affords 100% light protection was selected.

EXAMPLE 3

In Vitro Percutaneous Absorption of ($^{14}$C)-Menadione Study #1

Simultaneously with the stability evaluation of the prototypes presented in Table 3, a second set of prototypes was prepared and evaluated for their ability to deliver menadione into the viable epidermal and dermal layers. Menadione in Dimethyl Sulfoxide (DMSO) was run as a positive control as it is well known to be an optimal skin penetration enhancer.

The samples were initially prepared at 0.1% (w/w) Menadione and subsequently spiked with 0.1% (w/w) ($^{14}$C)-Menadione to achieve tested 0.2% (w/w) concentration of Menadione. The study was conducted using excised human skin from a single donor obtained following elective surgery using Bronaugh Flow-Thru diffusion cells.

Skin samples were exposed to the prototype sample for 24 hours. Following exposure of the skin samples to the formulations, the degree of penetration was measured as radioactivity in the tape-strip, epidermis, dermis and receptor fluid samples, using liquid scintillation analyzing techniques.

The composition of the evaluated prototype samples and results of their respective skin permeation values are presented in Table 16.

TABLE 16

Composition and Percutaneous Absorption of Menadione Prototypes

| Ingredients | % w/w | | | | | | | | | |
|---|---|---|---|---|---|---|---|---|---|---|
| | 1 | 2 | 3 | 4 | 5 | 13 | 6 | 8 | 11 | 14 |
| Menadione, USP | 0.1 | 0.1 | 0.1 | 0.1 | 0.1 | 0.1 | 0.1 | 0.1 | 0.1 | 0.1 |
| ($^{14}$C)-Menadione | 0.1 | 0.1 | 0.1 | 0.1 | 0.1 | 0.1 | 0.1 | 0.1 | 0.1 | 0.1 |
| Diethyl Sebacate | 3.0 | — | — | — | — | — | 10.0 | 10.0 | 15.0 | — |
| Diisopropyl Adipate | — | 6.0 | — | — | — | — | — | — | — | — |
| Isopropyl Myristate, NF | — | — | 12.0 | 12.0 | 12.0 | 12.0 | — | — | 50.0 | — |
| White Petrolatum, USP | — | — | — | — | — | 5.0 | 5.0 | 5.0 | — | — |

TABLE 16-continued

Composition and Percutaneous Absorption of Menadione Prototypes

| Ingredients | % w/w | | | | | | | | | |
|---|---|---|---|---|---|---|---|---|---|---|
| | 1 | 2 | 3 | 4 | 5 | 13 | 6 | 8 | 11 | 14 |
| Light Mineral Oil, NF | — | — | — | — | — | — | — | — | 34.8 | — |
| Brij 72 | — | — | — | — | — | — | 3.5 | — | — | — |
| Brij 721 | — | — | — | — | — | — | 1.5 | — | — | — |
| Emulsifying Wax | — | — | — | — | — | — | — | 12.0 | — | — |
| Pemulen TR-1, NF | 0.3 | 0.3 | 0.3 | 0.3 | 0.3 | 0.3 | — | — | — | — |
| Carbopol 981, NF | 0.1 | 0.1 | 0.1 | 0.1 | 0.1 | 0.1 | 0.1 | — | — | — |
| Methylparaben, NF | 0.17 | 0.17 | 0.17 | — | — | — | — | 0.17 | — | — |
| Propylparaben, NF | 0.03 | 0.03 | 0.03 | — | — | — | — | 0.03 | — | — |
| Benzyl Alcohol, NF | — | — | — | 1.0 | 1.0 | 1.0 | 1.0 | — | — | — |
| Propylene Glycol, USP | — | — | — | — | 5.0 | 20.0 | — | — | — | — |
| Dimethyl Sulfoxide | — | — | — | — | — | — | — | — | — | 99.8 |
| 4% NaOH Solution | | | | q.s. pH ~5.0-6.0 | | | | — | — | — |
| Phosphate Buffer | — | — | — | — | — | — | — | q.s. pH ~5.0-6.0 | — | — |
| Purified Water | | | | q.s. ad 100 | | | | | — | — |
| Average Percutaneous Absorption in Values of Percent of Applied Dose, N = 5 | | | | | | | | | | |
| Tape Strips | 7.2 | 4.9 | 6.7 | 11.2 | 7.4 | 3.9 | 37.5 | 36.3 | 20.6 | 4.36 |
| Epidermis | 30.1 | 33.0 | 35.7 | 40.6 | 32.9 | 32.9 | 25.1 | 25.6 | 31.3 | 36.4 |
| Dermis | 11.1 | 12.7 | 14.2 | 18.9 | 13.6 | 10.4 | 9.13 | 9.12 | 14.2 | 17.0 |
| Receptor Phase | 30.0 | 25.6 | 31.4 | 38.1 | 31.3 | 36.3 | 17.3 | 21.9 | 23.4 | 44.3 |
| Average Skin Deposition of Menadione (mM), N = 5 | | | | | | | | | | |
| Epidermis | 1.06 | 1.16 | 1.26 | 1.43 | 1.16 | 1.16 | 0.88 | 0.90 | 1.10 | 1.28 |
| Dermis | 0.129 | 0.147 | 0.165 | 0.220 | 0.158 | 0.122 | 0.106 | 0.106 | 0.165 | 0.197 |

The percutaneous absorption results presented in Table 16 demonstrate that all of the evaluated prototypes provide adequate permeability, as all of them delivered more than 10% of the applied dose through the skin over a period of 24 hours. The epidermal concentrations were in the range of 0.88 to 1.43 mM exceeding the original goal of an estimated delivery range between 0.1 to 0.5 mM. From this data, it was apparent that the menadione concentration in the formulation could be reduced by a factor of at least four (to 0.05%) and provide an adequate concentration of menadione in the epidermal skin layer.

All formulations evaluated demonstrated adequate permeability properties; therefore the formulation selection was based mainly on physical and chemical stability as well as the physical attributes of the target formulation(s). With reference to Table 3, the following Table 17 contains a presentation of the rationale for the selection of the lead and back-up formulations.

TABLE 17

Rationale for Lead and Back-up Formulation Selection

| Formulation | Disposition | Rationale |
|---|---|---|
| 1 | Back Up Formulation | After 3 months at all conditions the formulation was physically and chemically stable. The formulation also demonstrated good skin permeability properties based on the in vitro percutaneous absorption study. As the drug solvent diethyl sebacate is non-compendial this formulation was selected as the back up formulation to formulation 4. Subsequently after 6 months at 25° C. and 40° C. large oil droplets were observed indicating physical instability. |
| 2 | Alternate Back Up Formulation | After 3 months at all conditions the formulation was physically and chemically stable. The formulation also demonstrated good skin permeability properties based on the in vitro percutaneous absorption study. This formulation was chosen as a back up to formulation as it appeared to be slightly tacky when applied to the skin. |
| 3 | Consider for future development if appropriate | This formulation showed good chemical and physical stability at all conditions after 3 months. The formulation is similar to formulation 4 with the exception of the preservative system. Formulation 3 uses a methylparaben/ propylparaben preservative system whereas formulation 1 uses a benzyl alcohol preservative system. Benzyl Alcohol was preferred as the preservative as it has a better safety profile than the parabens. |
| 4 | Lead Formulation | After 3 months the formulation was physically and chemically stable. The physical appearance of the product stored at 40° C. changed from a yellowish lotion to a darker shade of yellow. Despite the color change, the sample retained its chemical integrity, as evidenced by the chemical potency remaining within acceptable limits. |

TABLE 17-continued

Rationale for Lead and Back-up Formulation Selection

| Formulation | Disposition | Rationale |
|---|---|---|
| | | The formulation met all the primary objectives:<br>a. Ethyl Alcohol-free product<br>b. Compendial formulation components<br>c. Vehicle composed of FDA approved excipients<br>d. Chemically stable<br>e. Physically stable<br>f. Highly spreadable and cosmetically elegant<br>g. Pharmaceutically acceptable attributes<br>h. Preserved product<br>In addition, formulation 4 demonstrated good skin permeability properties based on the initial in vitro percutaneous absorption study. |
| 5 | Not Selected | After 3 months at 40 C a significant loss of assay was observed indicating chemical instability. |
| 6 | Not Selected | After 3 months at 40° C., phase separation was observed indicating physical instability. |
| 7 | Not Selected | After 1 month at 40° C., phase separation was observed indicating physical instability. |
| 8 | Consider for future development if appropriate | Although this formulation was physically and chemically stable at all conditions after 3 months, due to the high emulsifying wax content a significant waxy residue was left on the skin. It was also not readily spreadable which may not be suitable for application over a large body surface area. |
| 9 | Not Selected | After 1 month at 40° C., phase separation was observed indicating physical instability. |
| 10 | Not Selected | After 1 month at 40° C., phase separation was observed indicating physical instability. |
| 11 | Consider for future development if appropriate | Although this formulation was physically and chemically stable at all conditions after 3 months, the formulation was significantly oily and greasy when applied to the skin. It was decided that this physical attribute was not optimal. |
| 12 | Consider for future development if appropriate | Although this formulation was physically and chemically stable at all conditions after 3 months, the formulation was significantly oily and greasy when applied to the skin. It was decided that this physical attribute was not optimal. |

Based on the rationale provided in Table 17, formulation 1 and formulation 4 were carried forward for an additional in vitro percutaneous absorption study in addition to a primary packaging compatibility study.

EXAMPLE 4

In Vitro Percutaneous Absorption of ($^{14}$C)-Menadione Study #2

The purpose of this second in vitro study was to characterize the in vitro percutaneous absorption of ($^{14}$C)-Menadione at concentrations of 0.05, 0.1, and 0.2%. These studies were conducted with lead formulation 4 and the backup formulation 1 following topical application to dermatomed, normal human skin obtained following elective surgery.

Percutaneous absorption of ($^{14}$C)-Menadione was also evaluated using abraded human skin in the lead formulation at 0.05, 0.1, and 0.2% Menadione and the backup formulation at 0.2% Menadione. Abraded skin was evaluated as a possible simulation of the type of broken and/or compromised skin that may be present in the case of a skin rash caused by an EGFR inhibitor. The respective skin permeation values are presented in: Table 18.

TABLE 18

Percutaneous Absorption of Menadione

| | | | | | % w/w | | | | | |
|---|---|---|---|---|---|---|---|---|---|---|
| Formul. | −1 (0.05%) $N^1$ | −1 (0.1%) $N^1$ | −1 (0.2%) $N^1$ | −1 (0.2%) $A^2$ | −4 (0.05%) $N^1$ | −4 (0.1%) $N^1$ | −4 (0.2%) $N^1$ | −4 (0.05%) $A^2$ | −4 (0.1%) $A^2$ | −4 (0.2%) $A^2$ |
| Average Percutaneous Absorption in Values of Percent of Applied Dose, N = 5 | | | | | | | | | | |
| Tape Strips | 8.87 | 6.24 | 5.21 | 7.05 | 4.71 | 5.97 | 5.19 | 4.01 | 2.49 | 3.20 |
| Epidermis | 33.4 | 32.7 | 29.8 | 13.4 | 35.8 | 28.6 | 25.2 | 27.6 | 20.3 | 18.6 |
| Dermis | 7.35 | 10.1 | 12.3 | 14.1 | 13.8 | 13.4 | 12.6 | 17.4 | 13.1 | 13.8 |
| Receptor Phase | 19.6 | 22.7 | 28.2 | 47.0 | 16.7 | 19.1 | 24.3 | 28.2 | 39.1 | 37.6 |

TABLE 18-continued

Percutaneous Absorption of Menadione

| | | | | | % w/w | | | | | |
|---|---|---|---|---|---|---|---|---|---|---|
| Formul. | −1 (0.05%) $N^1$ | −1 (0.1%) $N^1$ | −1 (0.2%) $N^1$ | −1 (0.2%) $A^2$ | −4 (0.05%) $N^1$ | −4 (0.1%) $N^1$ | −4 (0.2%) $N^1$ | −4 (0.05%) $A^2$ | −4 (0.1%) $A^2$ | −4 (0.2%) $A^2$ |
| Average Skin Deposition of Menadione (mM), N = 5 | | | | | | | | | | |
| Epidermis | 0.29 | 0.58 | 1.05 | 0.47 | 0.32 | 0.50 | 0.89 | 0.24 | 0.36 | 0.66 |
| Dermis | 0.017 | 0.046 | 0.113 | 0.129 | 0.032 | 0.062 | 0.116 | 0.040 | 0.060 | 0.126 |

[1]N notates normal skin
[2]A notates abraded skin

In summary, efficiency of ($^{14}$C)-Menadione skin permeation increased with increasing concentration of API in the formulations. There was no significant difference in the efficiency of ($^{14}$C)-Menadione skin permeation observed with Formulation 1 compared to Formulation 4 at comparable concentration of menadione and skin condition (normal or abraded). Little difference was noted in epidermal levels of menadione between the two formulations at comparable concentration of menadione. The epidermal levels of the drug were observed to be lower when applied to abraded skin. However, this observation is probably of little clinical significance since measured epidermal levels are typically associated with compound presence in stratum corneum, and also because the abrasion increased the overall penetration of menadione to the receptor, which indicates more menadione passed into and through the epidermis in the case of abraded skin. Abrading the skin prior to application of the test formulations significantly increased ($^{14}$C)-Menadione skin permeation efficiency, suggesting greater delivery of menadione (and potential clinical activity) when applied to damaged skin.

EXAMPLE 5

Primary Packaging Stability Study

A primary packaging stability study was evaluated using a new batch of the lead formulation 4 at 0.2% and 0.1% menadione for 12 months, and the back up formulation 1 at 0.2% menadione for 3 months, respectively. These two formulations were filled into aluminum tubes selected as the packaging component, with a 30 g capacity, equipped with a blind end, end sealant and a white high density polyethylene (HDPE) piercing cap. The tubes have a PE-1090-21 internal lacquer coating, and are supplied by Montebello (Part no.: 0/7/8/S/L-DO9005-SP60).

The packaged products were placed in 5° C., 25° C., and 40° C. storage, protected from light and a second experiment at ambient conditions allowed exposure to ambient room light. The physical and chemical stability of the lead and back up formulation prototypes at each condition are presented in Table 19 to Table 21.

TABLE 19

Physical and Chemical Stability of the Lead Menadione Topical Lotion, 0.2% in Aluminum Tubes

| Formulation 4 (Lead) | Appearance | pH (neat) | Viscosity (cps)[1] | Assay by HPLC (% of LC) |
|---|---|---|---|---|
| Interval | | 5° C./dark | | |
| t = 0 mo | Light yellow lotion | 5.4 | 4,650 | 96.7 |
| t = 1 mo | Not evaluated | | | 98.4 |

TABLE 19-continued

Physical and Chemical Stability of the Lead Menadione Topical Lotion, 0.2% in Aluminum Tubes

| Formulation 4 (Lead) | Appearance | pH (neat) | Viscosity (cps)[1] | Assay by HPLC (% of LC) |
|---|---|---|---|---|
| t = 3 mo | Light yellow lotion | 5.3 | 4,390 | 97.2 |
| t = 6 mo | Light yellow lotion | 5.2 | 4,870 | 97.7 |
| t = 12 mo | Light yellow lotion | 5.2 | 4,800 | 100.4 |
| Interval | | 25° C./dark | | |
| t = 0 mo | Light yellow lotion | 5.4 | 4,650 | 96.7 |
| t = 1 mo | Light yellow lotion | 5.3 | 4,340 | 96.8 |
| t = 3 mo | Light yellow lotion | 5.4 | 4,230 | 96.9 |
| t = 6 mo | Light yellow lotion | 5.3 | 4,440 | 97.1 |
| t = 12 mo | Light yellow lotion | 5.3 | 4,340 | 100.2 |
| Interval | | Ambient Temperature/Ambient Light | | |
| t = 0 mo | Light yellow lotion | 5.4 | 4,650 | 96.7 |
| t = 1 mo | Light yellow lotion | 5.3 | 4,370 | 98.0 |
| t = 3 mo | Light yellow lotion | 5.4 | 4,230 | 98.1 |
| t = 6 mo | Light yellow lotion | 5.2 | 4,610 | 97.5 |
| t = 12 mo | Light yellow lotion | 5.3 | 4,520 | 101.4 |
| Interval | | 30° C./dark | | |
| t = 0 mo | Light yellow lotion | 5.4 | 4,650 | 96.7 |
| t = 3 mo | Slight deepening in yellow color | 5.4 | 4,230 | 97.1 |
| t = 6 mo | Slight deepening in yellow color | 5.2 | 3,880 | 97.1 |
| t = 12 mo | Slight deepening in yellow color | 5.3 | 2,980 | 100.6 |
| Interval | | 40° C./dark | | |
| t = 0 mo | Light yellow lotion | 5.4 | 4,650 | 96.7 |
| t = 1 mo | Light yellow lotion | 5.3 | 3,960 | 97.7 |
| t = 3 mo | Slight deepening in yellow color | 5.3 | 3,130 | 96.2 |
| t = 6 mo | Deepening in yellow color | 5.3 | 2,520 | 95.6 |

[1]Viscosity Parameters: Spindle 27, Speed 30 rpm

TABLE 20

Physical and Chemical Stability of the Lead Menadione Topical Lotion, 0.1% in Aluminum Tubes

| Formulation 4 (Lead) | Appearance | pH (neat) | Viscosity (cps)[1] | Assay by HPLC (% of LC) |
|---|---|---|---|---|
| Interval | 5° C./dark | | | |
| t = 0 mo | Light yellow lotion | 5.3 | 5,090 | 98.8 |
| t = 1 mo | Not evaluated | | | 99.4 |
| t = 3 mo | Light yellow lotion | 5.3 | 4,780 | 98.2 |
| t = 6 mo | Light yellow lotion | 5.3 | 5,200 | 96.7 |
| t = 12 mo | Light yellow lotion | 5.4 | 5,240 | 99.1[2] |
| Interval | 25° C./dark | | | |
| t = 0 mo | Light yellow lotion | 5.3 | 5,090 | 98.8 |
| t = 1 mo | Light yellow lotion | 5.3 | 4,780 | 98.6 |
| t = 3 mo | Light yellow lotion | 5.3 | 4,580 | 98.5 |
| t = 6 mo | Light yellow lotion | 5.3 | 4,900 | 96.5 |
| t = 12 mo | Light yellow lotion | 5.3 | 4,500 | 99.7 |
| Interval | Ambient Temperature/Ambient Light | | | |
| t = 0 mo | Light yellow lotion | 5.3 | 5,090 | 98.8 |
| t = 1 mo | Light yellow lotion | 5.3 | 4,800 | 101.4 |
| t = 3 mo | Light yellow lotion | 5.3 | 4,630 | 99.2 |
| t = 6 mo | Light yellow lotion | 5.3 | 4,980 | 98.5 |
| t = 12 mo | Light yellow lotion | 5.4 | 4,800 | 100.1 |
| Interval | 30° C./dark | | | |
| t = 0 mo | Light yellow lotion | 5.3 | 5,090 | 98.8 |
| t = 3 mo | Slight deepening in yellow color | 5.2 | 4,280 | 99.2 |
| t = 6 mo | Slight deepening in yellow color | 5.3 | 4,320 | 96.5 |
| t = 12 mo | Slight deepening in yellow color | 5.4 | 3,630 | 98.5 |
| Interval | 40° C./dark | | | |
| t = 0 mo | Light yellow lotion | 5.3 | 5,090 | 98.8 |
| t = 1 mo | Light yellow lotion | 5.3 | 4,420 | 99.7 |
| t = 3 mo | Slight deepening in yellow color | 5.2 | 3,600 | 98.0 |
| t = 6 mo | Deepening in yellow color | 5.3 | 3,700 | 94.8 |

[1]Viscosity Parameters: Spindle 27, Speed 30 rpm

TABLE 21

Physical and Chemical Stability of the Back-Up Menadione Topical Lotion, 0.2% in Aluminum Tubes

| Formulation 1 (Back-Up) | Appearance | pH (neat) | Viscosity (cps)[1] | Assay by HPLC (% of LC) |
|---|---|---|---|---|
| Interval | 5° C./dark | | | |
| t = 0 mo | Yellow lotion | 5.4 | 4,060 | 97.1 |
| t = 1 mo | Not evaluated | | | 97.7 |
| t = 3 mo | Conforms | 5.4 | 3,930 | 97.1 |
| Interval | 25° C./dark | | | |
| t = 0 mo | Yellow lotion | 5.4 | 4,060 | 97.1 |
| t = 1 mo | Conforms | 5.4 | 3,860 | 97.7 |
| t = 3 mo | Conforms | 5.4 | 3,730 | 98.8 |
| Interval | Ambient Temperature/Ambient Light | | | |
| t = 0 mo | Yellow lotion | 5.4 | 4,060 | 97.1 |
| t = 1 mo | Conforms | 5.4 | 3,890 | 95.6 |
| t = 3 mo | Conforms | 5.4 | 3,700 | 99.6 |
| Interval | 40° C./dark | | | |
| t = 0 mo | Yellow lotion | 5.4 | 4,060 | 97.1 |
| t = 1 mo | Conforms | 5.4 | 3,590 | 96.8 |
| t = 3 mo | Slight deepening in color | 5.3 | 2,480 | 94.3 |

[1]Viscosity Parameters: Spindle 27, Speed 30 rpm

As shown in Table 19 and Table 20, the lead formulation remained physically and chemically stable under all conditions evaluated. Throughout the evaluation, parameters such as appearance, pH, viscosity and potency remained within the acceptable limits. Under the 40° C. condition a deepening in color and a reduction in viscosity was observed over time.

As shown in Table 21, the back-up formulation remained physically and chemically stable under all conditions evaluated. Throughout the evaluation, parameters such as appearance, pH, viscosity and potency remained within the acceptable limits. Under the 40° C. condition a deepening in color and a reduction in viscosity was observed over time.

For both the lead and back up formulations it can be seen that after 12 months at ambient condition exposed to ambient room light there was no significant change in the chemical or physical properties. This indicates that the primary packaging system provides 100% protection of the product from light and was therefore selected for the packaging of the non-clinical and clinical batches.

EXAMPLE 6

Clinical Formula Composition

Based on the adequate permeability of formulation 4 from both in vitro percutaneous absorption studies and its respective physico-chemical stability in borosilicate glass and in the primary packaging study, the compositions listed in Table 22 were selected for non-clinical and clinical evaluations.

TABLE 22

Clinical Formula Composition

| Ingredients | % w/w | % w/w | % w/w |
|---|---|---|---|
| Menadione, USP | 0.2 | 0.1 | 0.05 |
| Isopropyl Myristate, NF | 12.0 | 12.0 | 12.0 |
| Pemulen TR-1, NF | 0.3 | 0.3 | 0.3 |
| Carbopol 981, NF | 0.1 | 0.1 | 0.1 |
| Benzyl Alcohol, NF | 1.0 | 1.0 | 1.0 |
| Sodium Hydroxide, NF | 0.08[1] | 0.08[1] | 0.08[1,] |
| Purified Water, USP | 86.32[1] | 86.42[1] | 86.47[1] |

[1]Estimated Quantity

All excipients used in Menadione Topical Lotion are of the USP or NF grade. All ingredients are also listed in and are within acceptable ranges per FDA's Inactive Ingredient Guide (IIG) for topical products. The comparison of excipients to IIG acceptance limits are listed in Table 23.

TABLE 23

Comparison of Excipients to IIG Acceptance Limits

| Ingredient | % w/w | Maximum Use Levels (IIG) |
|---|---|---|
| Isopropyl Myristate, NF | 12.0 | 35% |
| Benzyl Alcohol, NF | 1.0 | 50% |
| Pemulen TR-1, NF | 0.3 | 1.5% |
| Carbopol 981, NF | 0.1 | 0.85% |
| Sodium Hydroxide, NF | 0.06 | 10% |

The function of each excipient is listed in Table 24.

TABLE 24

Function of Excipients Used in Menadione Topical Lotion

| Ingredient | Grade | Use |
|---|---|---|
| Isopropyl Myristate | NF | Solvent/Emollient |
| Benzyl Alcohol | NF | Preservative |
| Carbopol 981 | NF | Gelling Agent |
| Pemulen TR-1 | NF | Emulsifier/Gelling Agent |
| Sodium Hydroxide | NF | Neutralizer |
| Purified Water | USP | Carrier |

Carbopol 981 conforms to the Carbomer 941, NF monograph. Pemulen TR-1 conforms to the Carbomer Copolymer and to the Carbomer 1342 NF monographs. Both polymers are benzene free. The FDA's Inactive Ingredient Guide refers to these materials as Carbomer 981 and Carbomer 1342, respectively.

Placebo Formulation for Menadione Lotion

Since the active component, menadione, is a yellow powder, and since Menadione Topical Lotion therefore has a light yellow appearance due to the menadione component, a known amount (7 ppm) of FD&C yellow #5 is dissolved in the water phase to maintain an appearance comparable to that of the drug product. The remaining ingredients in the formulation are the same as those described in Example 7. A stability study was initiated to evaluate the physical and chemical stability of the Placebo for Menadione Lotion formulation. The Placebo for Menadione Lotion formulation was compounded in borosilicate clear glass vials. All vials were stored at 5° C. (dark), 25° C. (dark) and 40° C. (dark) to assess the stability of the placebo formulation. The physical and chemical stability results are provided in Table 25.

TABLE 25

Physical and Chemical Stability of Placebo for Menadione Lotion

| Lot 2560-13A | Appearance | pH (neat) | Viscosity (cps)[1] |
|---|---|---|---|
| Interval | 5° C./dark | | |
| t = 0 mo | Yellow lotion | N.T | N.T |
| t = 3 mo | Yellow lotion | 5.1 | 4,700 |
| t = 6 mo | Yellow lotion | 5.2 | 4,700 |
| Interval | 25° C./dark | | |
| t = 0 mo | Yellow lotion | N.T | N.T |
| t = 3 mo | Yellow lotion | 5.1 | 4,400 |
| t = 6 mo | Yellow lotion | 5.2 | 4,300 |
| Interval | 40° C./dark | | |
| t = 0 mo | Yellow lotion | N.T | N.T |
| t = 3 mo | Yellow lotion | 5.2 | 3,800 |
| t = 6 mo | Yellow lotion | 5.2 | 3,700 |

N.T = Not Tested

[1]Viscosity Parameters: Spindle 21, Speed 60 rpm

EXAMPLE 7

Batch Formulations for Use in Clinical Studies

Three 37.5 Kg clinical Menadione Topical Lotion batches were manufactured at concentrations of 0.2%, 0.1% and 0.05%. The clinical supplies were packaged in 60 g aluminum tubes with blind end, end sealant and a black polypropylene (PP) piercing cap. The tubes have a PE-1090-21 internal lacquer coating, and are supplied by Montebello (Part no.: 1/1/4/S/L-HA1020-SP22). During development, the cap color was changed from white to black because it was surprisingly discovered that use of white caps allowed light penetration into the product after breaking the seal, resulting in product deterioration in the area around the neck of the tube that received the minimal light exposure. This is in accordance with stability observations as noted in Table 7, for example.

The respective batch formulas are provided in Table 26 to Table 28.

TABLE 26

Menadione Topical Lotion, 0.2% Batch Formula

| Ingredients | Quality Standard | % w/w | Batch Quantity (g)[3] |
|---|---|---|---|
| Menadione | USP | 0.20 | 75.0 |
| Isopropyl Myristate | NF | 12.00 | 4,500.0 |
| Benzyl Alcohol | NF | 1.00 | 375.0 |
| Pemulen TR-1 | NF | 0.30 | 112.5 |
| Carbopol 981 | NF | 0.10 | 37.5 |
| Sodium Hydroxide | NF | 0.08[1,2] | 30.0[1,2] |
| Purified Water | USP | 86.32[1] | 32,370.0[1] |

[1]Estimated Quantity
[2]Sodium Hydroxide solution added to q.s. pH 5.5-6.0
[3]Quantity per batch for a 37.5 Kg Batch

TABLE 27

Menadione Topical Lotion, 0.1% Batch Formula

| Ingredients | Quality Standard | % w/w | Batch Quantity (g)[3] |
|---|---|---|---|
| Menadione | USP | 0.10 | 37.5 |
| Isopropyl Myristate | NF | 12.00 | 4,500.0 |
| Benzyl Alcohol | NF | 1.00 | 375.0 |
| Pemulen TR-1 | NF | 0.30 | 112.5 |

TABLE 27-continued

Menadione Topical Lotion, 0.1% Batch Formula

| Ingredients | Quality Standard | % w/w | Batch Quantity (g)[3] |
|---|---|---|---|
| Carbopol 981 | NF | 0.10 | 37.5 |
| Sodium Hydroxide | NF | 0.08[1,2] | 30.0[1,2] |
| Purified Water | USP | 86.42[1] | 32,407.5[1] |

[1]Estimated Quantity
[2]Sodium Hydroxide solution added to q.s. pH 5.5-6.0
[3]Quantity per batch for a 37.5 Kg Batch

TABLE 28

Menadione Topical Lotion, 0.05% Batch Formula

| Ingredients | Quality Standard | % w/w | Batch Quantity (g)[3] |
|---|---|---|---|
| Menadione | USP | 0.05 | 18.75 |
| Isopropyl Myristate | NF | 12.00 | 4,500.00 |
| Benzyl Alcohol | NF | 1.00 | 375.00 |
| Pemulen TR-1 | NF | 0.30 | 112.50 |
| Carbopol 981 | NF | 0.10 | 37.50 |
| Sodium Hydroxide | NF | 0.08[1,2] | 30.00[1,2] |
| Purified Water | USP | 86.47[1] | 32,426.25[1] |

[1]Estimated Quantity
[2]Sodium Hydroxide solution added to q.s. pH 5.5-6.0
[3]Quantity per batch for a 37.5 Kg Batch Placebo Lotion for Menadione Additionally, one 37.5 Kg clinical Placebo batch was manufactured. The batch formula is provided in Table 29.

TABLE 29

Placebo Lotion for Menadione Batch Formula

| Ingredients | Quality Standard | % w/w | Batch Quantity (g)[3] |
|---|---|---|---|
| Isopropyl Myristate, NF | USP | 12.00 | 4,500.00 |
| Benzyl Alcohol, NF | NF | 1.00 | 375.00 |
| FD&C Yellow #5 | Supplier Standard | 0.0007 | 0.26 |
| Pemulen TR-1, NF | NF | 0.30 | 112.50 |
| Carbopol 981, NF | NF | 0.10 | 37.50 |
| Sodium Hydroxide, USP | NF | 0.08[1,2] | 30.00[1,2] |
| Purified Water, USP | USP | 86.5193[1] | 32444.74[1] |

[1]Estimated Quantity
[2]Sodium Hydroxide solution added to q.s. pH 5.5-6.0
[3]Quantity per batch for a 37.5 Kg Batch

EXAMPLE 8

Clinical Formulations

Menadione Topical Lotion, containing concentrations of 0.05%, 0.1%, or 0.2% (w/w), can be used for treatment of rash secondary to epidermal growth factor receptor inhibitor (EGFRi) therapies and other skin conditions. The product is essentially a yellow to light yellow lotion with target pH of 5.5 to 6.0 and a viscosity of approximately 3,000 to 4,000 cps using the following viscosity parameters, Spindle 27, Speed 30 rpm. The formulation is specifically designed to facilitate complete dissolution of menadione drug substance in the oil-phase and to maintain its overall solubility of either 0.05%, 0.1% or 0.2% menadione (w/w) in the lotion formulation.

Manufacturing Process Development

The manufacturing process for Menadione Topical Lotion, 0.05%, 0.1%, or 0.2%, is conducted under yellow light to prevent the degradation of the active pharmaceutical ingredient (API) as it is known to be photosensitive, and subsequently the deterioration of the finished product.

The compounding process is typical of commercial scale manufacturing of emulsions. The oil phase and aqueous phase are prepared separately, heated to 70° C., and are then combined with high shear mixing to form an emulsion. Upon cooling, the emulsion is additionally thickened by raising the pH to a range of 5.5-6.0 by the addition of a 2% sodium hydroxide solution to produce a homogeneous product.

Container Closure System

Information on the container closure is provided below in Table 29.

TABLE 29

Container Closure System

| Container | Dimensions | Material/Internal Coating | Crimp Sealant | Manufacturer | Part Number | Use |
|---|---|---|---|---|---|---|
| 60-g capacity, white aluminum tube with blind end, and a black polypropylene (PP) piercing cap | Body Length with cap: 5.25 inches Tube outer diameter: 1.25 inches | 1170 Alloy/PE-1090-21 internal lacquer coating | Darex CMPD AD 2311B LS | Montebello Packaging 1036 Aberdeen St. Hawkesbury, Ontario K6A 1K5 Canada | 1/1/4/S/L-HA1020-SP22 | Clinical batches |

Microbiological Attributes

Based on formulation development experience using benzyl alcohol as a preservative in topical formulations, benzyl alcohol was selected as the preservative system in the menadione formulations. Subsequent anti-microbial effectiveness testing (AET) has demonstrated the effectiveness of the preservative system in the selected lead formulation. The Menadione Topical Lotion, 0.2% passed the USP and EP/BP requirements of the AET test. Acceptable AET results for the 0.2% formulation means that the same formulations containing less menadione (for example, 0.05% and 0.1%) are also acceptable.

Compatibility

An LDPE applicator commercially available for delivery of various similar products will be used to facilitate accurate clinical dosing. The expected contact time between the candidate drug product and the applicator is not expected to exceed 5 minutes.

EXAMPLE 9

Characterization of Menadione Topical Lotion for the Prevention and Treatment of Skin Toxicities Associated with EGFR Inhibitor Therapy Background: Acneform rash is a pervasive, painful, and treatment-limiting complication of EGFR inhibitor therapy with reported incidence rates ranging from 50-100%. Menadione Topical Lotion (MTL) is being developed as a targeted treatment for this side effect of EGFR inhibitors, of which there are 4 approved agents (erlotinib, gefitinib, panitumumab and cetuximab). Menadione has been shown to have direct EGF activating activity as well as EGFR and other growth factor-related phosphatase inhibitory activity.

Methods: This Phase 1, placebo-controlled, open-label, modified dose-escalation study assessed the bioavailability, safety and tolerability of three concentrations (0.05%, 0.1%, 0.2%) of MTL and placebo administered BID on face, neck, upper chest and upper arms of subjects for 3.5 days in a 7 day cycle over a 28 day period. The pharmacokinetic parameters of MTL were assessed in blood and tissue and the major metabolites menaquinone-4 and thiodione were assessed in blood. Potential response biomarkers p27, p63 and pEGFR, were measured in skin.

Results: Twelve normal subjects, 6 male and 6 female, with a median age of 43 years (range, 30-52) were entered into the study. Plasma drug levels were analyzed and negligible plasma menadione concentrations near the lower limit of quantification were observed in a small sample of patients. This confirms that topical menadione has no significant systemic absorption. The most frequent adverse events (AEs) potentially related to MTL included skin toxicities of erythema and a burning sensation. All AEs were CTC Grade 1 or 2. Immunohistochemical analysis of p27, p63 and pEGFR suggest that normal skin structure and signaling was not adversely affected by MTL.

Conclusions: Pharmacokinetic analysis of plasma from MTL treated subjects demonstrated insignificant systemic levels of menadione and its major metabolites menaquinone-4 and thiodione. MTL is being developed for EGFR inhibitor therapy-associated skin toxicity (rash) and is currently under investigation in a Phase 1 study in cancer patients receiving EGFR inhibitor therapy.

Equivalents

Throughout this specification the disclosures of various publications, the full citations of which were referred to in parenthesis, are hereby incorporated by reference in their entireties into the subject application to more fully describe the art to which the subject application pertains.

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A topically applicable pharmaceutical formulation suitable for treatment of a dermatological condition comprising,
   a) from about 0.01 to 2% (w/w) of menadione;
   b) from about 1 to 50% (w/w) of a lipophilic component selected from the group consisting of isopropyl myristate, caprylic/capric triglyceride, diethyl sebacate, diisopropyl adipateand combinations thereof;
   c) from about 0.01 to 5% (w/w) each of one or more acrylic acid based polymers;
   e) from about 0.03 to 10% (w/w) of a preservative;
   f) a neutralizing agent sufficient to maintain a pH of about 4.0 to 7.0; and
   g) water;
   wherein the formulation delivers a concentration of about 0.1 to 1.5 mM vitamin K3 to the epidermal skin layer when applied topically.

2. The pharmaceutical formulation of claim 1 comprising,
   a) from about 0.05 to 2% (w/w) of menadione;
   b) from about 3 to 20% (w/w) of the lipophilic component selected from the group consisting of isopropyl myristate, caprylic/capric triglyceride, diethyl sebacate, diisopropyl adipateand combinations thereof;
   c) from about 0.1 to 1.0% (w/w) each of one or more acrylic acid based polymers;
   e) from about 0.5 to 5% (w/w) of the preservative;
   f) a neutralizing agent sufficient to maintain a pH of about 4.5 to 6.5; and
   g) purified water;
   wherein the formulation delivers a concentration of about 0.1 to 1.5 mM vitamin K3 to the epidermal skin layer when applied topically.

3. The pharmaceutical formulation of claim 1, comprising
   a) about 0.05 to 0.2% (w/w) menadione;
   b) about 12% (w/w) isopropyl myristate;
   c) about 0.3% (w/w) Acrylates/C10-30 Alkyl Acrylate Crosspolymer;
   d) about 0.1% (w/w) prop-2-eonic acid carbomer;
   e) about 1% (w/w) benzyl alcohol;
   f) sodium hydroxide sufficient to maintain a pH of about 5.0 to 6.0; and
   g) purified water.

4. The pharmaceutical formulation of claim 1, comprising
   a) about 0.05 to 0.2% (w/w) menadione;
   b) about 3% (w/w) diethyl sebacate;
   c) about 0.3% (w/w) Acrylates/C10-30 Alkyl Acrylate Crosspolymer;
   d) about 0.1% (w/w) prop-2-eonic acid carbomer;
   e) about 0.3% (w/w) each of methylparaben and propylparaben;
   f) sodium hydroxide sufficient to maintain a pH of about 5.0 to 6.0; and
   g) water.

5. The pharmaceutical formulation of claim 1, comprising
   a) about 0.05 to 0.2% (w/w) menadione;
   b) about 6% (w/w) diisopropyl adipate;
   c) about 0.3% (w/w) Acrylates/C10-30 Alkyl Acrylate Crosspolymer;
   d) about 0.1% (w/w) prop-2-eonic acid carbomer;

e) about 0.3% (w/w) each of methylparaben and propylparaben;
f) sodium hydroxide sufficient to maintain a pH of about 5.0 to 6.0; and
g) water.

6. A packaged pharmaceutical formulation comprising the pharmaceutical formulation of -any one of claims 1 to 5 in a light impermeable container.

7. The pharmaceutical formulation of any one of claims 1 to 5, wherein the formulation is ethyl alcohol free.

8. The pharmaceutical formulation of claim 1, comprising about 0.05 to 2% (w/w) vitamin K3.

9. The pharmaceutical formulation of claim 1 or 2, comprising about 0.01 to 0.5% (w/w) vitamin K3.

10. The pharmaceutical formulation of claims 1 or 2, comprising about 0.01 to 0.2% vitamin K3.

* * * * *